United States Patent [19]
Filler et al.

[11] Patent Number: 5,614,652
[45] Date of Patent: Mar. 25, 1997

[54] PARTICULATES

[75] Inventors: Aaron G. Filler, Seattle, Wash.;
Andrew M. Lever, Cambridge, United Kingdom

[73] Assignee: Syngenix Limited, Cambridge, England

[21] Appl. No.: 87,781

[22] PCT Filed: Jan. 4, 1992

[86] PCT No.: PCT/EP92/00021

§ 371 Date: Oct. 5, 1993

§ 102(e) Date: Oct. 5, 1993

[87] PCT Pub. No.: WO92/11846

PCT Pub. Date: Jul. 23, 1992

[30] Foreign Application Priority Data

| Jan. 7, 1991 | [GB] | United Kingdom | 9100233 |
| Jan. 16, 1991 | [GB] | United Kingdom | 9100981 |
| Jan. 31, 1991 | [GB] | United Kingdom | 9102146 |
| May 20, 1991 | [GB] | United Kingdom | 9110876 |
| Jul. 30, 1991 | [GB] | United Kingdom | 9116373 |
| Aug. 19, 1991 | [GB] | United Kingdom | 9117851 |
| Aug. 30, 1991 | [GB] | United Kingdom | 9118676 |
| Sep. 13, 1991 | [GB] | United Kingdom | 9119665 |

[51] Int. Cl.$^6$ .............. C07F 15/00; C07F 15/02
[52] U.S. Cl. .................. 556/136; 556/138
[58] Field of Search ............. 424/1.61; 556/136, 556/138

[56] References Cited

U.S. PATENT DOCUMENTS

| 4,101,435 | 7/1978 | Hasegawa et al. | 252/62.53 |
| 5,001,014 | 3/1991 | Charles et al. | 428/473 |

FOREIGN PATENT DOCUMENTS

| 3711724 | 4/1987 | Denmark . |
| 9007322 | 7/1990 | WIPO . |

OTHER PUBLICATIONS

Speiser, Peter P. (1991) "Nanoparticles and Liposomes: A State of the Art" Methods and Findings in Experimental and Clinical Pharmacology 13(5):337–342.

Toshiba Glass Co., Ltd. (1989) Patent Abstracts of Japan 13(496):127 E 843, Abstract No. 1–200605.

Primary Examiner—Cynthia Harris Kelly
Attorney, Agent, or Firm—Saliwanchik & Saliwanchik

[57] ABSTRACT

There is provided a means of cellular level therapy or prophylaxis whereby endocytosable particles are administered so as to emit cytotoxic radiation or to release metal cations having a therapeutic or prophylactic effect, eg. a vital replication suppressing effect, within cells such as macrophages following their uptake by these cells.

1 Claim, 13 Drawing Sheets

PARTICULATES

This invention relates to the use of particulate agents in therapeutic or prophylactic treatments of conditions involving cellular infection or malfunction.

Many human and animal diseases involve infection or malfunction of the body's cells, eg. by virtue of viral, bacterial (eg. mycobacterial) or protozoal infection or cancerous malfunction. While the body's immune system is generally able to cope with foreign matter, it is not always able to recognise and destroy cells which have become infected or have begun to malfunction. This is particularly serious in the case of certain infections where the pathogen may remain dormant within infected cells for prolonged periods and also where, as for instance is the case with HIV infection, by infecting cells of the immune system the disease weakens the body's ability to defend itself.

Besides vital infection where the parasite is obliged to replicate within a host cell, the range of known intracellular pathogens is wide and includes the pathogens associated with tuberculosis, listeria, Crohn's disease and leprosy as well as brucella, rickettsias and legionella.

Much of the research effort directed at the development of therapeutic agents for the treatment of such diseases has been directed towards the production of complex organic chemicals which on the whole are not very efficiently delivered into the infected or at-risk cells.

The present invention is based on the realisation that effective delivery of inorganic active agents may be achieved by administration of particulate agents incorporating the active inorganic agent where the particles are of a size that permits their endocytosis, or more especially phagocytosis. This administration route is especially attractive since, unlike complex and chemically more delicate organic drugs, inorganic agents and in particular metal cations and radionuclides will generally not be particularly susceptible to loss of activity as a result of exposure to the relatively harsh chemical environments commonly experienced during or following endocytotic particle uptake.

Thus viewed from one aspect the invention provides the use of a physiologically tolerable, preferably inorganic, material containing atoms or ions of a therapeutically or prophylactically effective element for the manufacture of a particulate agent containing said element, said agent being for use in a therapeutic or prophylactic treatment of the human or animal body which involves delivery of said particles or fragments thereof into cells of said body by endocytosis.

Viewed from a further aspect the invention provides a method of prophylactic or therapeutic treatment of the human or animal, preferably mammalian, body said method comprising administering into said body a particulate agent comprising particles of a physiologically tolerable, preferably inorganic, material containing atoms or ions of a therapeutically or prophylactically effective element whereby to deliver said particles or fragments thereof into cells within said body by endocytosis.

Viewed from a still further aspect, the invention provides a pharmaceutical composition comprising endocytosable particles of a physiologically tolerable, preferably inorganic, material containing atoms or ions of a therapeutically or prophylactically effective element together with at least one pharmaceutical carrier or excipient.

In order that delivery of the "active" element into body cells by endocytosis may be achieved, the particles which effectively serve as a carrier for the active element will generally be substantially insoluble in the body fluids that they are to encounter between administration into the body and endocytosis by the targeted cells. Some diminution in particle size can be tolerated of course and if desired particles may of course be provided with protective coatings or disintegrants so as to ensure that particles of desired sizes are present at or throughout the body zone at which endocytotic uptake is desired or so as to ensure that endocytosable particles are present at such sites for a prolonged period of time.

Administration may be by any route which delivers the particles to body sites at which endocytosis by the targeted cells may take place. This will of course depend on the type of cell that is being targeted, which in turn depends upon the condition that is being treated or against which prophylactic treatment is being given. However in general administration into the systemic vasculature, into the musculature, topically or into body cavities having external voidance ducts (in particular into the vagina or, by inhalation, into the lungs for access to pulmonary alveolar macrophages) will be the preferred routes.

When particles are injected intravenously in humans or animals they are swept from the blood stream relatively rapidly, e.g. within a few hours, by endocytosis by monocytes and macrophages or they are endocytosed by circulating peripheral blood monocytes. This has been demonstrated for $^{59}$Fe labelled particles of mixed particle size (20–100 nm) injected into a rabbit. Serial 1 ml blood samples were taken from a vein in the ear and as shown by the decreasing radiation count shown in FIG. 7 approximately 50% clearance was achieved within 2 hours. Particle uptake in this fashion by spleen, liver, lymph nodes, lung, and by the Langerhans cells, after topical application by vaginal macrophages and by monocyte lineage cells in the marrow, by microglia of the central nervous system and by gastrointestinal tract lymphoid tissue, is a well known phenomenon and in certain cases has been utilised as a means of improving image contrast for various organs in diagnostic imaging techniques by the administration of particulate contrast agents, for example the superparamagnetic ferrite particles used as $T_2$ contrast agents in magnetic resonance imaging of liver and spleen tumours. In this regard particle distribution to and slow breakdown in other types of macrophages and monocytes has hitherto been viewed as an undesirable aspect of the particles' biodistribution.

However in the case of diseases associated with infection or malfunction of particle endocytosing cells, this pattern of distribution can be seen to be most fortuitous if the particles are used to deliver therapeutically or prophylactically effective agents into those cells.

This is of particular importance in the cellular level therapy or prophylaxis of diseases in which macrophages are liable to infection, especially mycobacterial and retroviral infections, as it is well known that as macrophages succumb to infection, for example HIV infection, they can still engage in the "non-specific" phagocytosis of particles long after they lose the ability to selectively ingest C3 or Fc bearing structures.

Thus macrophages and monocytes, which are a principal reservoir, incubation site and pathogenic target of diseases such as HIV, retain, even up to the latest stages of pathological change, their ability to ingest the particles used according to the invention and thus their ability to receive into the cell the therapeutically or prophylactically active elements contained in those particles.

The delivery of the particles used according to the invention to their targeted cells may not only be affected by the administration route but also by modification of the medium in which the particles are administered, the size, coating or packing of the particles or by surface modification of the particles to promote uptake by particular cell types.

Thus for example to gain access to CNS macrophages for intravenously administered particles it may be desirable to reduce the effectiveness of the blood brain barrier, eg. by intravenous administration of an agent such as mannitol either simultaneously with or, preferably, in advance of administration of the particles. To this end, one may conveniently administer mannitol, eg. in 20% aqueous solutions, at a dose of 1 g/kg bodyweight.

Similarly, cell adhesion molecules (CAMs) or molecular fragments may be coupled to the particle surface to promote uptake by the targeted cells. By appropriate selection of the labelling CAM, or by selection of a range of CAMs, one may ensure that particles are preferentially endocytosed (phagocytosed) by cells which are uninfected (but liable to infection) or by infected cells at different stages of infection. Since different active elements may exert different cytotoxic or pathogen replication suppressing effects, this may be used as a means to achieve a combined therapeutic and prophylactic treatment or to effect a therapeutic treatment against a combination of pathogens or against one pathogen at several of its replicative stages.

CAMs may typically be used in two ways to improve the selectivity of particle uptake and so direct them to the sub-populations of macrophages that are or are not actually infected. If a mixture of particles is administered, some conjugated with CD4 (or the gp120 binding site) while others are unconjugated or conjugated with Fc the first set will tend to be phagocytosed by HIV infected cells while the second will tend to be taken up by uninfected cells. Alternatively using smaller particles which are phagocytosed much more slowly if at all, these may be conjugated with immunoadhesions or anti-gp120 antibody and they will enter infected cells via an immunologic route as well as by phagocytosis. Additionally the $gp^{120}$ protein itself or the gp120/gp41 HIV envelope complex with or without a mutation in the fusion peptide of gp41 or the CD4 binding site of the gp120 protein alone may be conjugated to the particles so that they will mimic the selectivity of the HIV virus and so preferentially enter CD4 positive cells.

Besides being endocytosable by macrophages and monocytes, the particles used according to the invention may be endocytosed by other infected or at-risk cells or by cancerous (malfunctioning) cells. Particularly interestingly it has been shown that therapeutically/prophylactically effective particles may be taken up by cells such as nerve cells, sarcoma cells and T-cells, including Jurkat T-cells stably expressing the HIV-1 tat gene.

The "active element" in the particles used according to the invention will generally be a radionuclide capable of exerting a cytotoxic effect on particle/radiation emission or, more preferably, a metal which in cationic form interferes with the initiation or progression of the cellular infection of concern or with the metabolism of a malfunctioning cell. In this latter case of cation cell therapy, the efficacy of the technique is closely linked to the difference between the relatively effective mechanisms that the host animal's (e.g. human's) cells have for either tolerating or deactivating (e.g. by chelation or isolation) the therapeutic metal cations as compared with the relatively poor ability of the infecting organism to protect itself from the therapeutic cations. This efficacy also derives at least in part from differences in the equilibrium or affinity constants of various enzymes, proteins, and other biomolecules for the therapeutic cations.

In the case of cellular infection, eg. retroviral infection or mycobacterial infection, it is possible to use particles according to the invention which on intracellular breakdown release metal cations that interfere with the metabolism or replication of the infectious agent, eg. by interfering with the functioning of the reverse transcriptase (RT) enzyme that is vital to retroviral replication. The $Mg^{2+}$ dependence of RT, the $Mn^{2+}/Mg^{2+}$ dependence of RNase H and the conserved cysteine rich/CCHC "zinc finger" sites on the gag protein and the cystein rich dimerization site of the tat protein are thus all potential targets for cation cell therapy to inhibit HIV infectivity.

The use of inorganic crystallites, e.g. ceramic metal oxide crystal matrices, which breakdown gradually in the chemical environment encountered within the endocytosing cell allows gradual, slow intracellular release of the physiologically active element by a relatively non-toxic mechanism. Such a slow release mechanism means that "drug" administration may be relatively infrequent, e.g. weekly, fortnightly, or monthly.

While cation cell therapy will be exemplified below with particular reference to HIV therapy it should be borne in mind that other intracellular pathogens are also susceptible to such treatments and the choice of appropriate cations, cation mixtures and cation loading levels within the particles used according to the invention may be made on the basis of relatively straight-forward laboratory tests, for example in vitro tests showing the response of the particular pathogenic agent to the metal ions/metal ion mixtures in question. Thus by way of example the response of retroviruses other than just HIV, eg. SIV, MoMuLV and AMV, may be monitored in vitro by an RT assay.

The range of metals that can be loaded into endocytosable particles to effect cation cell therapy according to the invention is extremely large, indeed virtually any metal can be delivered this way. Metals which occur naturally in the target cells may be considered as well as metals which compete with naturally occurring cations or which effect a suppressive effect on the pathogen in other ways. Thus cation cell therapy may be used to create a broad range of selectively altered intracellular cationic milieux, e.g. by altering the concentration of a cation which is normally present or by providing an alternative cation, and investigations suggest that in many instances the infective agent is more susceptible to such manipulation than is the host cell.

The acquired immune deficiency syndrome (AIDS) is caused by infection of certain human cell types by the Human Immunodeficiency Virus (HIV). A variety of drug strategies have been developed which target various aspects of the viral infection and pathogenic sequence; however there are no effective treatments or cures for AIDS infection. All those infected are expected to die from the disease and currently that includes tens of millions of people throughout the world.

Most current, single agent treatments now under investigation involve small molecules such as nucleoside analogs or protein antibodies. However, the cells particularly affected by HIV are naturally active in attacking large particles, including particles similar in size to the virus, and the anti-HIV treatment particles of the invention take advantage of this natural feature of these cells. Further, given the high pathogenicity of HIV and its ability to evolve relatively rapidly, attention should be directed towards multiple lines of attack in a single treatment, and this invention provides further ways of combining multiple points of attack in a single particulate agent. Indeed in general the particles used according to the invention may be provided with a coating which comprises one or more organic drugs and so be used in a combined therapy whereby the organic drug acts in concert or synergistically with the active element contained in the particle.

HIV is a retrovirus, meaning that its genetic information is encoded in RNA rather than DNA. It has a glycoprotein coat which is quite variable in structure. However, one of its coat proteins called gp120 has an invariable region which recognises and binds to an antigen called CD4 and this appears to be a key to the disease process.

CD4 occurs on T helper lymphocytes and on a variety of related cells in the monocyte group. These monocytes include blood monocytes, reticuloendothelial system (RES) cells such as splenic macrophages, liver Kuppfer cells, lymph node dendritic cells, Langerhans cells in various locations, alveolar macrophages in the lungs, and microglia and related phagocytic cells in the central nervous system and together form a principal location of the HIV infection.

When an HIV virus gp120 coat protein comes in contact with a CD4+ cell, it binds to it and so causes a conformational change exposing the fusogenic domain of the associated gp41 envelope glycoprotein which fuses with the cell membrane of the human CD4+ cells, and so introduces the virus into the interior of the cell. There, the virus reverse transcriptase (RT) enzyme is activated, a DNA copy of the viral RNA is made, and that viral DNA is intercalated into the cell's normal DNA. Once intercalated, the viral DNA is read repeatedly under the transcriptional control of the viral "tat" (transactivator of transcription) protein and the viral rev (regulator of expression of virion) protein to produce large quantities of viral protein transcript and viral RNA. Via a series of protease and protein modification steps, new viral particles are generated.

During this process, multiple copies of gp120 appear in the cell membrane and may bind to the CD4 antigen on uninfected macrophages. The infected cell can then bind to and fuse with the uninfected cell and so doom that cell as well. Syncytia of multiple captured monocytes are formed in this fashion. Also, during this process, CD4 bearing T-cells and other T-cells may approach the infected monocyte and so, by contact, become infected by the virus.

To date, the only successful pharmaceutical treatment for HIV infection is AZT which is an analog of one of the constituent nucleosides of the viral genetic material. This drug hinders the viral replication process and so slows the progress of the disease. However, it is not curative and its associated toxicity has led to an intensive further search for drugs which can act synergistically with it. Also, there have been reports of new strains of HIV which are resistant to AZT. There are a variety of other dideoxynucleoside analogs which may be similarly efficacious and these are being actively investigated.

There are three principal new drug strategies. One involves some analogs of the benzodiazepine drug family (HIPO) which have been discovered during massive screening programs which have sought anti-viral activity from huge numbers of compounds. The exact mechanism of action is not clear, but, as with AZT, the formation of viral DNA by reverse transcriptase seems to be the point of action. These and related drugs are being actively explored.

A second new strategy has resulted from the discovery that sulfated dextran molecules may irreversibly bind viral particles. This has led to related discoveries of a number of sulfated polymer molecules which can adsorb viral particles. The best way to use such agents is not yet clear; if they bind a virus but are then swept into monocytes along with the virus, they may actually enhance the infectivity of the virus.

The third group of strategies involves immunology and genetically engineered proteins focused on the CD4+ protein and its receptor on the gp120 molecule. The CD4 protein or relevant portions thereof will attach to HIV and it will attach to gp120 where it is presented on the surface of infected cells. Simply administering soluble CD4 should block the gp120 recognition site and may thus prevent cellular infection by individual viruses.

CD4 can also be used as a delivery vehicle to deliver a cytotoxic agent selectively to infected cells. Thus in one approach, recombinant CD4 is attached to pseudomonas exotoxin so as to deliver this powerful cellular toxin to infected cells. A similar approach attaches CD4 to ricin, a poisonous plant lectin. Genentech has proposed an 'immunoadhesin' molecule which is a hybrid between a recognition/targeting portion composed of the region of CD4 that binds gp120, and, a cytotoxic portion from the human antibody Fc region—the portion that triggers cytotoxic attack in e.g. bacterial infection after antibody binding.

For all of these CD4 related strategies, there has been the problem of providing sufficient cytotoxicity with an administered toxin without harming the patient too severely, or, in the case of the immunoadhesin, of how to stimulate a vigorous attack on the infected monocytes when the patient's Fc based cytotoxic system is compromised—the very essence of AIDS.

While there are numerous drugs under investigation for the treatment of AIDS and while there are a variety of prior uses of particulate agents, eg. metal oxide particles, there has hitherto been no suggestion of the use of particles to achieve cellular level cation therapy or short range radiotherapy by endocytotic uptake. Thus for example, this is the first use of metal oxide particles for the treatment of any viral infection; it is also the first use of β-emitter particles or of Auger electron radiation for the treatment of an HIV infection; this is also the first use of metal oxide ceramic particles as a means of delivering slow release selective metal cation inhibitors of reverse transcriptase; and further, it is the first application of spinel mediated microwave diathermy to the treatment of AIDS.

The particles used according to the invention may be of virtually any physiologically tolerable material; as mentioned above however they will generally be of a material which is substantially insoluble in extracellular body fluids, in particule serum or plasma. Organic matrices (eg. natural or synthetic, essentially inert, organic polymer particles such as dextran coated microspheres or latex nanospheres) may be used but particularly preferably the particles will be inorganic, especially alloys and metal sulphides or oxides as these may break down naturally within the cells to release the metal cations active in the cation cell therapy aspect of the invention.

Many metal oxide structures may be utilized as the inorganic particles, and spinels, garnets and perovskites have been found to be particularly useful in this regard. It should however be stressed that other well known inert and preferably essentially water insoluble metal compounds may be used, especially those having lattices such as permit desired metal cations or radioisotopes to be included. By alloys, mixed metals are of course included.

In a preferred embodiment, the particles comprise a core metal oxide crystal, eg. of spinel or garnet structure, if desired coated for example by dextran carbohydrate, wherein the total size of the particle is 5 nm to 15 μm, preferably 10 nm-5 μm, especially 10 nm-1μm, particularly 10–100 nm, more particularly 10 to 50 nanometers and most especially 20–30 nm, and where a targeting moiety (TM) is optionally bound to the coating at a concentration of TM per particle which may for example be as low as about 1:1. Where TM labelling is used to achieve highly specific uptake of the particles by particular cell types, by cells infected by particular agents or by infected cells at particular stages of infection, it may be desirable that the agent be virtually free of particles lacking an active TM. For particles smaller than 100 nm, the particle compositions are preferably sterilized by 0.2 or 0.1 micron microfiltration after final synthesis, affinity purification and concentration. Otherwise, heat sterilization may be used prior to conjugation to any targetting moiety, e.g. protein or protein fragment.

The uses of a given version of a particulate metal oxide agent depend upon the elements and isotopes (radionuclides) used in the initial precipitation step in which the metal oxide crystal core is precipitated and also upon the types of coating and targeting moiety that may be used. For each use, the metals/nuclides, coatings and targeting moieties may be selected to benefit both from the general advantages of the simplicities of the preparatory method and to take advantage of the new types of pharmaceutical distribution which can be achieved by materials prepared in this way.

In cationic cell therapy of retroviral infection according to the invention one can have an attack on the $Mg^{2+}$ dependence of RT on two parallel strategies—by delivering a competing metal ion into the cytosol free or bound to a phosphate moiety of a nucleotide. Most metal ions at physiological pH tend to cause hydrolysis which results in their precipitation as polymeric hydrous oxides. However, it has proven possible in vitro to use scandium as a magnesium antagonist in several enzyme systems. This trivalent first row transition metal is effectively non-toxic although its only known clinical use is as a bacteriostatic agent.

The trivalent lanthanide elements including scandium (Sc), yttrium (Y), and lanthanum (La) in the IIIB group as well as the fourteen chemically similar rare earths of the lanthanide series have been extensively exploited over the past twenty years in studies of the interactions of divalent cations with their physiological enzyme substrates. Except for scandium, most have ionic radii similar to that of calcium and have been useful in studies of various active sites since they provide a gradually progressive array of charge/surface densities.

Scandium, however, in addition to being the least toxic of the entire group, is similar to magnesium in ionic radius, reduction potential, and electronegativity, differing primarily in its stable 3+ oxidation state. Scandium has recently been exploited because of its similarity to aluminium, and this work has led to better appreciation of its solution chemistry.

Replacement of $Mg^{2+}$ with $Sc^{3+}$ in muscle actin has been demonstrated. However, the demonstration that $Sc^{3+}$ acts as a competitive antagonist of $Mg^{2+}$ in one of the two $Mg^{2+}$ sites on the beta-adrenergic receptor-adenylate cyclase complex of the murine S49 lymphoma cell is also most interesting. Since $Sc^{3+}$ and $La^{3+}$ have similar affinities for ATP but different effects on the adenylate cyclase, it was possible to rule out the generation of non-productive ScATP- as the cause of the inhibition. The effect at the $Mg^{2+}$ site responsible for activation but not at the site responsible for agonist selectivity also served to demonstrate that the inhibition by $Sc^{3+}$ was due to a specific interaction at an $Mg^{2+}$ site on the enzyme rather than to some non-specific metal/protein interaction.

In some bacterial DNA polymerases, there are as many as 21 sites for divalent cations per enzyme molecule with the binding affinity and importance for enzymatic function varying widely among the sites. The number and function of RT cation sites for HIV or other retroviruses are not completely understood, although it is clear that there are differences among closely related Group C retroviruses in cation preference and that incomplete dimer structure of HIV RT may result in distinctive roles for such cations. Possibilities for cation dependency are further extended by the demonstration of two manganese/magnesium cation sites in the RNAse H portion of the HIV RT protein.

For these reasons, for cation cell therapy according to the invention consideration may be given to using $Sc^{3+}$, $y^{3+}$, and $La^{3+}$, as well as several other heavier lanthanides and, because of the preference of other polymerase enzymes for $Mn^{2+}$ rather than $Mg^{2+}$, other metal ions of the first and second row transition metals. The ions of interest include $Co^{2+}$, $Ni^{2+}$, $Cu^{2+}$, and $Zn^{2+}$ and from the second row, $Ru^{3+}$, and $Pd^{2+}$. Lithium and strontium also deserve consideration.

Accordingly in one embodiment of the present invention there are used as particles for cation cell therapy particles which on degradation will release a retroviral replication suppressing, eg. RT activity inhibiting, metal ion. Experiments on the effects of various metal ions on RT activity have been carried out and the majority of mono, di and trivalent metal cations were found to influence RT activity. The influence is dependent on the element and its concentration as well as on the particular viral infection under study. For HIV RT, divalent ions appeared especially efficacious, in particular Pd, Zn, Cu and Ni and of these most especially Pd. While scandium and sixth series trivalent metal ions exhibit RT activity inhibiting effects with some viruses, they seem to be less effective with HIV.

Cationic cell therapy may also be achieved by interference with zinc-binding sites; thus panels of metal ions (eg. Cd, Co, Cu, Fe, Hg, Mn, Zn) have been explored previously by various researchers in attempts to characterise the function and structure of $Cys-X_2-Cys-X_4-His-X_4-Cys$ (CCHC) and other cysteine-rich, putatively metal binding conserved sequences occurring in several HIV proteins. The functional importance of zinc binding to some of these sites remains unclear.

Mutations in the CCHC sequence in the gag protein result in the production of non-infectious viral particles which do not carry genomic RNA. The enhancer proteins HIV-EP1 and HIV-EP2 which cause viral activation upon binding the NF-$_\kappa$B site enhancer on the HIV-1 LTR both include classical Xenopus TFIIIA zinc binding sites. The tat protein is dimerized by the action of zinc or cadmium at its conserved cysteine rich region and mutations in that region interfere with viral replication. The inventors have also demonstrated that tat function is altered when Jurkat-tat T cells endocytose and digest particles carrying substitute metal cations such as $Pd^{2+}$. Because of this complex multiple involvement of various sites which either require zinc or which are conserved but may physiologically or pathologically bind zinc, it is necessary, having selected the target virus, to carry out relatively straightforward in vitro tests to select the appropriate concentration and mix of metal cations to optimise effective interference with the proteins and the pathogenic effects of the infecting organism.

For this reason and others, the general cellular response to digested particles as a source of introduced cations may be used to assess their effectiveness when the digesting cells are infected by or are subsequently exposed to a selected pathogenic organism. This is conveniently achieved by involving the preparation of unconjugated or CD4-conjugated particles for phagocytosis by cultured human monocytes or cultured T-cells which are then infected, e.g. with HIV; where the cell line chosen is one susceptible to synctium formation this may then be used as an assessment of infectivity.

Among the primary candidates for competition are those metal cations whose tetracoordinate complexes are similar in ionic radius to tetracoordinated zinc. These include $Pd^{2+}$ and $Li^{1+}$ which together provide a range of ionic radii. The previous metal panels assessed suggested that larger ions may be accommodated more readily than ions which are too small.

Palladium has an ionic radius and coordination chemistry quite similar to manganese and, when included in an organic chelate complex, it has long been known to inhibit retroviral reverse transcriptase. However, there have been no clinical uses for palladium cations because there has been no way to deliver such cations selectively to infected cells in sufficient amounts without causing very high systemic levels.

When palladium is included in particles administered to HIV infected patients a very useful distribution is achieved. Even with no specific directing antigen, these particles will be swept up by the macrophage system. In this fashion, uninfected macrophages will be made to ingest and slowly to degrade the particles. These cells can therefore be made to have a long term steady state release of intracellular palladium. This will confer protection effective against retroviral infection because it will inhibit the function of the reverse transcriptase of any entering virus as well as having various other effects.

In this fashion, relatively high intracellular levels of this protective element can be achieved in those cells most subject to attack. In combined therapy with β-emitting particles, palladium is used in a portion of the mix of particles conjugated with an indifferent antigen or with Fc since it is helpful in the uninfected cells of infected patients.

When various concentrations of active cations, eg. active transition cations, are used in assays of reverse transcriptase activity, three general patterns of response are found: 1) the cation proves irrelevant to the enzyme and does not activate, but also permits full activation by the subsequent addition of magnesium; 2) the cation fully or partially activates the enzyme and the subsequent addition of magnesium has either no or little effect or actually decreases the enzyme activity; or 3) the cation does not activate the enzyme and subsequently prevents activation by magnesium. One additional pattern is demonstrated by cations which 4) activate the enzyme when present in low concentration but actually inhibit it and prevent magnesium activation when present in higher concentration. Similar expectations apply for $Ag^{2+}$ and various other metal cations.

These four patterns are exhibited by various cations, but the effect of any given cation on RT activity is dependent on the strain and species of the virus involved. The results for the retrovirus Moloney Murine Leukemia Virus (MoMuLV) show pattern 1 for lithium and strontium, pattern 2 for cobalt and manganese, pattern 3 for copper, nickel, palladium, scandium and the lanthanides, and pattern 4 for zinc.

A different array of activities is seen for Human Immunodeficiency Virus. For HIV, aluminium shows pattern 1, lithium and cobalt show pattern 2, copper, zinc, palladium, nickel and ruthenium show pattern 3, and manganese shows pattern 4.

When dextran coated cation sources are crystallised and prepared using $Mn^{2+}$, $Pd^{2+}$ and $Ni^{2+}$ as the divalent cation in spinel crystals, important effects on viral activity are seen. Concentrations of particles equivalent to 1 mg/ml of trivalent cation chloride hydrate were exposed to cultured human macrophage cells (THP-1 line) for periods of 1 or 2 hours to permit particle uptake, after which the cells were washed and placed in fresh medium. Twenty four hours later, a small infectious inoculum of the RF strain of HIV was introduced into the various culture wells and a variety of uninfected controls were also observed. At intervals of 3, 7, 11, and 14 days, cells were counted, viability assessed with trypan blue, and cell free supernatants were collected for reverse transcriptase assay.

The data obtained demonstrated that, relative to controls, Fe/Fe particles (i.e. ferrites in which the di- and trivalent metals are both iron) promote host cell growth and viability but do not affect viral spread or replication. Fe/Mn particles cause some impairment of cell viability but completely block HIV infection. Most usefully, the Fe/Ni and most strikingly the Fe/Pd particles have minimal effect upon or actually improve cell viability but cause dramatic or near complete suppression of HIV infectivity and so may be used therapeutically or prophylactically.

Besides providing a route to cellular level cation therapy of intracellular infection by HIV and the like which proceeds via cation competition interference with nucleic acid replication, the particulate endocytosis route provides a means by which cations may be administered into infected or infection susceptible cells so as to interfere with any selected stage of infection. Thus cations may bind directly to nucleic acids, form abnormal substrates (eg. $Me^{n+}$ ATP in place of $Mg^{2+}$ ATP, where $Me^{n+}$ is the therapeutic or prophylactic metal cation) or they may interfere with the polymerization of cytoskeletal or nucleocapsid proteins, change membrane characteristics, interfere with protein/nucleic acid interactions or reduce the availability of reactants necessary for proliferation of the pathogen.

Inorganic particles, eg. spinel particles, may be made to behave as stable aqueous colloids by precipitation from the metal salts in dextran solutions. By sulfating the dextran after precipitation, or by doing the precipitation with acrylic acid/polyvinyl alcohol sulfate, the special HIV adhesion property of these molecules can be conferred upon the particles. When such particles, or similar particles bearing conjugated CD4 or anti-gp120 are injected intravenously, they will sweep up any free viruses in circulation and carry them into already infected macrophages. As the particles degrade, the coating material will continue to have its inhibitory effect on vital replication within the cell.

Besides single cell cation therapy the invention also encompasses cellular level radiotherapy.

The intravenous administration of radiotherapeutic agents generally speaking has hitherto been limited to the use of small molecules. Where immune targeting is wanted, current techniques have generally involved coupling to an antibody a limited number of radioactive atoms, normally no more than one or two. The present invention however offers the possibility of synthesizing the particulate agent, eg. a spinel, with a high concentration of radiation emitting atoms.

By constructing large particles, eg. metal oxides containing positron emitters such as spinel positron emitters (SPE) or βelectron emitters it is possible to achieve great reduction of the range of the majority of the emitted positrons or electrons. Most of the cytotoxic ionizations will take place within 100–300 microns of the actual particle location with 50% taking place within less than 100 microns. Further, because of the Bragg peak effect, there will be substantial ionization yield even from those positrons which lose the majority of their energy within the particle.

Thus, any viruses adherent to the positron emitter containing particle will receive a very high dose rate of ionizating radition and many will be destroyed in this fashion. Once the particle is ingested by a monocyte, many of those cells, already doomed by infection, will die rapidly because of the radiation effect. If the half-life of the emitter is chosen to be in the range of 2–4 hours, eg. Scandium$^{43}$ then most of the activity will be expended before the cell dies and the particle is expelled for ingestion by another phagocytic cell. It is also possible to use an α-emitting nuclide such as Pt$^{186}$ for even greater toxicity if necessary. The particular value of an α-emitter is that it will be effective for only a very short range around the particle even when very small, non-moderating particles are synthesized. Finally, electron capture nuclides such as Palladium$^{103}$ can be used for their high dose/decay, very short range Auger electron cytotoxic effect. The decay characteristics of many radionuclides are known and appropriate radionuclei may be selected relatively easily—see for example "Periodic table of the elements", compiled by Fluck and Heumann, VCH, 1986.

Although the treatment of HIV infection is of tremendous concern, the methods described above as earlier noted are also applicable to a wide variety of other intracellular pathogens. Many of these pathogens are of heightened importance in the setting of AIDS, so that treatments which can simultaneously attack the AIDS virus as well as the other pathogens will be particularly useful. Intracellular pathogens of increased importance in the compromised host include: Histoplasmosis, Toxoplasmosis, Listeria, Candida, and Mycobacterium avium intercellulare complex. Other intracellular pathogens amenable to treatment by particles ingested by macrophages include Trypanosomes, Neisseria, Mycobacterium tuberculosis, Leishmania, Salmonella typhi, Legionella, Brucellosis, Ricketsia, Cytomegalovirus, Chlamydia, Shigella, some staphylococci, slow viruses or prions such as Creutzfeld-Jacob, Mycoplasma, herpes simplex, EBV, varicella zoster, or the papova virus associated with JC-type progressive multifocal levcoencephalopathy.

The inventors have for instance used cation source particles to influence the course of infection of human cells in culture by the HTLV-1 virus which causes both hematological cancer and also a focal myelopathy.

For any intracellular pathogen, conventional therapy is complicated by the relative inability of many drugs to achieve adequate intracellular doses. Thus, any pathogen which need not expose itself to the high antibiotic concentrations in the extracellular fluid, and which is also able to survive after ingestion by macrophages poses a serious risk to the infected host. Indeed many of the organisms mentioned in the previous paragraph continue to be terrible scourges even in the modern age of antibiotics.

Attacks on these various intracellular organisms have included the use of various drug carriers such as liposomes. However, the hydrophobic coating of these agents and the difficulties with targeting have limited success so far. Among the problems is the tendency for most particulate agents to be swept up by macrophages in the spleen and liver and then to fail to reach other macrophage compartments. The particles used according to the invention may be of a size or series or range of sizes and may carry targeting moieties such that more general or more specific endocytosis occurs. Thus using relatively small, eg. ca 10–50 nm, particles optionally provided with a hydrophilic coating, eg. a dextran coating, enables one to provide an efficient intracellular delivery vehicle for a broader range of macrophage sites. Further, many of these organisms are less able to tolerate abnormal concentrations of metal cations than are the host cells. Thus many of the considerations discussed above for cation therapy of HIV apply equally for these organisms.

A further consideration is the potential for including various antibiotic drugs in the particle coating along with or in place of the dextran coating. In AIDS patients, this permits cation cell therapy of HIV to be effected simultaneously with administration of high intracellular doses of specific antibiotics for opportunistic coinfecting organisms.

Further, where various cations interfere with function of viral, bacterial/yeast, and host functions, the addition of a specific antibiotic agent or antiviral agent (eg. AZT) can permit synergistic attack on the infecting organism while sparing the host cell from full bimodal attack.

In the course of exploring the sensitivity of control cell cultures to various mixed metal particle formulations, the inventors have learned that some formulations such as Fe/Mn mixed metal oxides tend to inhibit host cell growth without reducing cell viability. This sort of pharmacologic effect is the desired function of chemotherapeutic agents for cancer treatment. Since these particles have ready access to bone marrow, they provide a ready means of achieving intracellular therapy, both targeted and non-specific, for a variety of cancers where adequate phagocytic activity exists or can be induced. Experiments by the inventors have confirmed this alteration in cell culture growth kinetics in osteogenic sarcoma cells. Moreover, using $^{59}$Fe labelled dextran-coated metal oxide particles and electron microscopy it was confirmed that sarcoma cells do ingest the particles. In cellular level cancer therapy according to the invention, the clinical efficacy will derive in part from the sensitivity to cation substitution of the rapidly dividing cells and their mitotic machinery. Additionally, since for many cancers viruses and especially retroviruses play a causative role (see zur Hausen in Science 254:1167–1173 (1991)), the efficacy of cation cell therapy according to the invention will involve the effect of the therapeutic cations on the various stages of viral oncogenesis. Similar considerations apply in the therapeutic or prophylactic treatment of other virally influenced diseases such as for example multiple sclerosis.

Similar considerations also apply where there is an intention to depress host immune function for transplantation or to treat tissues to prevent graft versus host disease. Particulate cation therapy provides the opportunity to depress cell division for a limited period time without excessive toxicity.

Consideration of applicability for use in treating viral hepatitis involves differing strategies for the various subtypes. In Hepatitis B, the liver injury is due substantially to the inflammatory response to antigens presented on the surface of otherwise relatively healthy but infected hepatocytes. By introducing cation sources into local macrophages and other inflammatory cells, a local depression of the inflammatory process may be achieved although inhibiting the display of viral protein on the surface of such liver cells could be particularly effective. In other types of viral hepatitis such as C and D, the viral infection is cytopathic for the hepatocytes and cell surface receptors in a lipid coat for the cation source will aid in directing the particles into the hepatocytes rather than into macrophage cells.

Besides therapeutic and prophylactic uses, the particles used according to the invention may be useful in imaging procedures. Hitherto the imaging of HIV infection has been limited primarily to studies of the characteristic infections associated with AIDS. However, since the particulate agents according to the invention can be engineered to be visualizable as contrast agents upon X-ray computer tomographic (CT) scanning or magnetic resonance imaging (MRI), and can be detected upon magnetic resonance spectroscopy (MRS), positron emission tomography (PET) or single photon emission computer tomography (SPECT), it becomes possible to follow their distribution quite closely. For such uses, particles which are superparamagnetic or which incorporate appropriate metal atoms or radionuclides may conveniently be used. The opportunity to image infection sites, or more accurately to enhance image contrast in body zones in which the particles are endocytosed is of interest not only in studying and diagnosing the disease, but also in following the course of therapy and in the actual development and optimization of these agents.

There is a long history of use of magnetic particles for biochemical separations. For in vitro studies of the selectivity of the particles for infected as opposed to uninfected cells, it will be possible to prepare non-magnetic particles to be mixed with magnetic/CD4 particles. The targeted cells that have ingested the particles can then be separated from cells which have not ingested particles and then be assayed for presence of virus.

Where it is necessary to use radioactivity for various assays, MR spectroscopic properties of the particles can be used for non-interfering assessment of the particles themselves.

In vivo, it will be possible to use magnetized catheters such as central catheters in the atrium, to retrieve particles after their injection. In this fashion, particles coated with free viral particles can be removed from circulation as can any circulating monocytes which have ingested the particles. This is similar to a technique used for separating leukemic cells but would be a new use for viral infection in AIDS.

It has been known for some time that ferrimagnetic, ferromagnetic or superparamagnetic particles, eg. ferrite particles, can be synthesized so as to make them increase in temperature in response to radiation of selected wavelengths. This method had been difficult to apply for any actual medical uses because there has been no consistent motive or means to achieve intracellular distribution of the particles in cells which need to be killed. If however such particles are targeted upon HIV infected cells, eg. by surface labelling with CD4, the distribution question is well solved. The particles are given intravenously, and, because of CD4 conjugation, are selectively phagocytosed by infected monocytes and macrophages. After adequate distribution is achieved (one to two hours after injection), the patient can receive whole body irradiation with microwave frequencies tuned to activate just those particles with CD4 label. These particles can be heated sufficiently to have significant cytotoxic effect as well as synergistic effect with other concurrent cytotoxic treatments.

It will be appreciated that although the metals of the metal oxide, sulphide or alloy matrices of the inorganic particles of the invention may have naturally occurring radioisotopes, the particles used according to the invention for cellular level radiotherapy or for combined therapy and scintigraphic or PET imaging (where the radionuclide serves as a diagnostic marker for cells which endocytose the particles) will have significantly higher than natural abundance contents of the radioisotopes, e.g. for positron emitters an average of at least one, perhaps 10 or more atoms per 100 nm crystal. The natural occurrence of many $\beta^+$ emitters is less than 1 in $10^{20}$ and even one emitting atom per particle may suffice.

For other novel "doped" particles according to the invention, the therapeutically or prophylactively active or marker nuclei may be isotopes which occur naturally, e.g. as impurities in naturally occurring oxides, sulphides or alloys—in this case again the particles according to the invention will generally be distinguished by containing such atoms at higher than natural values, e.g. a hundred or even more per 100 nm particle.

The particles of the invention may be coated or uncoated and may derive their physiological tolerability at least in part from such a coating. They may moreover be coupled to a biotargetting moiety, for example an antibody, an antibody fragment, a CAM or a protein or protein fragment of a target pathogen, eg. a coating protein fragment such as from HIV's gp120.

The particles are preferably of a spinel or garnet structure—the manufacture of particles of these types is already well known and need not be described further here. By way of interest however it may be noted that superparamagnetic crystals of this type have been proposed for use as MRI contrast agents in various patent publications of Nycomed AS, Schering AG, Advanced Magnetics Inc, etc (eg. U.S. Pat. No. 4,863,715 (Jacobsen) and U.S. Pat. No. 4,827,945 (Groman)).

There are a wide variety of targeting moieties or CAMs which can be used according to the invention. These include antibodies, monoclonal antibodies, antibody fragments, receptors, peptides such as endorphins, steroid molecules, viral fragments or coat proteins, cell surface antigens including various carbohydrates, lectins, immunoadhesins, neurotransmitter molecules, growth factors, immunomodulators, prostacyclins, prostaglandins, interleukins, leukotrienes, and proteins or other molecules which promote endocytosis or uptake by other routes of the pharmaceutical agent by the target cells. The use of uncoated particles, eg. palladium ferrites, without any targeting moieties is nonetheless of very great interest.

The synthesis of metal oxide crystals as particulates in stable aqueous solution has been of interest in crystallography and in the paint pigment industry. However, many of the relevant advances have grown out of studies of magnetism.

Many of the agents described herein involve specially synthesized versions of magnetite ($Fe_3O_4$). The crystal structure of magnetite is based on a mineral called spinel $MgAl_2O_4$. However, when specific proportions of ferric and ferrous ions are used instead of magnesium and aluminum as the metal ions in the lattice: $Fe(II)(Fe(III))_2O_4$, a particular set of electronic alignments and exchanges are produced which result in spontaneous magnetization.

The basic structure of magnetite involves a close-packed, face centred cubic crystal of oxygen atoms with metal ions placed at interstitial spaces in the crystal. The interstices are divided into "A" sites and "B" sites which have different interstitial locations relative to the oxygen array and which therefore give rise to two distinct sub-lattices within the crystal. In the naturally occurring mineral "spinel" ($MgAl_2O_4$) the A-sites are filled by Mg(II) and the B sites by Al(III). The assignment of atoms to sublattices is determined in part by size. The A-sites allow atoms of 0.3 to 0.6 angstrom radius while the B-sites allow atoms of 0.6 to 1.0 angstroms. In a normal spinel crystal, the A-sites are filled by divalent atoms while the B-sites are filled by trivalent atoms.

Magnetite is an "inverse spinel" crystal because it has trivalent iron in its A-sites, and a mix of divalent and trivalent iron in its B-sites. Each crystal subunit has 32 oxygens, 8 A-site Fe(III) atoms, 8 B-site Fe(III) atoms and 8 B-site Fe(II) atoms. The general formula for spinel ferrites is Mt(II): $(Fe(III))_2(O)_4$, where Mt can be any divalent transition metal or a charge balanced mix of monovalent and trivalent metals of appropriate ionic radius.

The Fe(III) atoms in the A sublattice are positioned so as to oppose and cancel the spin magnetization of the Fe(III) in the B sublattice. However, after this cancellation, the 8 Fe(II) remaining in the B sublattice have completely unopposed spin magnetizations. For each $Fe_3O_4$ formula unit, there is a nee magnetization of 4 Bohr Magnetons due to the unopposed Fe(II) atoms. Each crystal subunit therefore has a magnetization of 32 Bohr Magnetons packed into a cube with a face that is 837 pm in length.

The magnetization of a ferrite can be altered by substituting different metals into the various interstices. For instance, Mn(II) has a magnetization of 5 Bohr Magnetons, so creation of an inverse spinel with the formula Mn(II)(Fe(III))$_2$O$_4$ should yield crystals with 5 Bohr Magnetons per unit. The use of Zn(II) has a quite different effect. It has no unfilled d-orbitals and so has zero magnetic moment. However, zinc tends to enter A sites causing a normal spinel organization for the crystal. Therefore, at each formula unit, a zero moment zinc opposes an Fe(III) with a moment of 5 Bohr Magnetons resulting in a net moment of 5 for the pair, the remaining Fe(III) are also unopposed, so the net moment is 10 Bohr Magnetons per formula unit (80 Bohr Magnetons per crystal subunit).

In actuality, this situation can prevail only for a low percentage of the total number of sites in a larger crystal. Zn(II) is actually too large for the A sites (0.77 angstrom radius) so that as the concentration of zinc exceeds 50%, there is a transformation into inverse spinel structure. In this arrangement, Fe(III) opposes Fe(III) cancelling each other out, and the unopposed Zn(II) have no moment, so the ferrite has a net magnetization of zero. This is sometimes useful in applications such as the heteronuclear tracers described below in which magnetization is not necessarily desirable.

In 1955 the term superparamagnetism was proposed to describe the behaviour of extremely small magnetic particles. The fundamental idea is that there is sufficient thermal agitation in a small particle that the tendency for the magnetic dipole axis to flip into various orientations is greater than the tendency to align as a coherent domain with a single fixed axis.

As the particle size increases above a critical size in the range of $10^6$ atoms, it becomes stable and coherently aligned as a spontaneously magnetized single domain. Below this critical size, the magnetic susceptibility is temperature and size dependent. Smaller particles at higher temperatures require stronger external fields to become detectably magnetized. Once magnetization is achieved, however, the total magnetization is related directly to the size of the particle.

The behaviour of a superparamagnetic particle is described by a relaxation rate which reflects the rate at which local magnetic moments within the particle will flip spontaneously. In order to flip, an energy barrier which is proportional to the volume of the particle and to the anisotropy of the material must be overcome. In a domain sized particle, the magnetization settles along one single axis because the energy barrier is too great to permit flipping at the temperature of the experiment. At sub-domain size, the energy barrier is low enough that the flip rate becomes exceedingly rapid. The size at which this transition occurs is temperature dependent and also dependent on the composition of the particle. (For present purposes the relevant temperature for determining whether or not a substance is superparamagnetic is body temperature).

By the substitution of some metals such as cobalt in place of some of the Fe(II) in the lattice, the crystals become more anisotropic and this tends to slow the rate of flipping and so lower the critical size for a stable domain.

When larger ions are included in the crystal matrix, the spinel structure cannot accommodate them. This is particularly important for the use of elements from the lanthanide series. However, lanthanides may be accommodated by the garnet crystal structure. The natural form of this crystal is Ca$_3$Al$_2$(SiO$_4$)$_3$ or 3CaO.Al$_2$O$_3$.3SiO$_2$. An analogous structure is achieved with the composition Ln$_3$Fe$_5$O$_{12}$, wherein Ln is a lanthanide element. (A common example made using Yttrium is called YIG or Yttrium-Iron-Garnet and is used for instance in lasers). Although small amounts of the lanthanides are accommodated within spinel crystals, stoichiometries which favour garnet formation are more important as larger percentages of lanthanides are included.

A novel type of spinel crystal uses scandium in place of aluminium in the preparation of coated, colloidal spinel crystals. The most stable of these are Mg(II)(Sc(III))$_2$O$_4$ or magnesium scandites. These are helpful vehicles in several of the applications described herein. These crystals are not magnetic. Scandium has stable trivalent chemistry but, unlike yttrium and lanthanides, is similar in ionic size to the remaining transition metals.

Methods for precipitating ferrites from metal salts date back into the 1800's and several investigators have modified these methods in attempts to develop improved ferrofluids. Elmore in Phys. Rev. 54: 309–310 (1938) explored ammonia precipitation of ultrafine ferrite particles in aqueous solutions and first demonstrated that their aggregation increased when they approached an applied magnetic field.

A further step towards developing stable colloidal ferrofluids came in 1965 with the development of a method for grinding magnetic materials into fine powders and then suspending them in oleic acid by sonication (see U.S. Pat. No. 3,215,572). Takada and Kiyama in Proc. Int. Conf. (ICF-1), U. Tokyo Press (Ed. Hoshino et al), p. 69–71 (1970) reexplored a variety of methods for precipitating ultrafine crystals of magnetite and developed a new oxidation method although this body of work did not address the problem of keeping the particles in suspension.

Reimers and Khalafalla in Bu Mines TPR 59:13 (1972) used an ammonia peptization method to create aqueous suspensions of ground particles. In their initial method, an acid treatment followed by sonication is used to induce interaction with solvent molecules to prevent clumping of the particles and maintain suspension. Subsequently, they developed a modification of Elmore's ammonia precipitation method to create more stable, dilutable suspensions in which molecules of dodecanoic acid are chemically adsorbed onto the surface of the magnetite particle (see Khalafalla and Reimers in IEEE Trans Mag 16: 178–183 (1980)). This yielded dilution-stable solutions of superparamagnetic particles.

Biologists became interested in small magnetic particles as potential means of carrying out biochemical separations and developed various means of incorporating domain sized particles into beads. These did not need to be soluble in the form initially used. However, building on methods used to create dense immunospecific labels for electron microscopy, an aqueous technique developed by Molday (see U.S. Pat. No. 4,452,773 and J. Immunol. Meth 52: 353–367 (1982)) opened the way to a variety of biological applications.

The Molday method involves an ammonia precipitation synthesis in which dextrans are used to coat the magnetite. This results in an aqueous suspension of superparamagnetic particles which can be conjugated to a wide variety of types of molecules including antibodies and so used to carry out various types of separations. The advantage of the superparamagnetism of the Molday particles is that they do not tend to aggregate magnetically unless they are in an applied magnetic field. This simplifies the preparation of more elaborate compounds while permitting recovering of the magnetic properties when they are wanted after the synthesis is completed.

Whitehead et al (U.S. Pat. No. 4,554,088) developed a silane binding technique in which clusters of superparamagnetic magnetite particles each about 30 nm in size are bound in groups into larger particles about 500 nm in diameter (now marketed as "AMI-25"). In the silane matrix, the small particles are held apart from each other and so retain their superparamagnetism. They therefore do not aggregate and remain relatively soluble. However, the total magnetic moment of the entire larger particle is quite large so that biological separations can be carried out.

Sub-micron coated iron oxide particles have been proposed for use as intravascular X-ray contrast agents and a number of other medical uses have been described for other superparamagnetic particles including magnetic confinement for blockage of fistulas and thrombosis of aneurysms, use in producing focal diathermy for treatment of infection, selective removal of tumour cells from bone marrow, and use as MRI contrast agents.

In the field of therapeutic/prophylactic particulate agents, the current invention achieves particular improved characteristics through the discovery that the use of repeated purification steps during the synthesis greatly improves the performance of the particles as biochemical reagents. These purifications remove dissolved metal ions as they appear during the synthesis since they can precipitate as hydrous oxides which impair the gel flow characteristics of the preparation during the synthesis. In addition, by using serial filtration steps after the initial precipitation, particles may be selected whose sizes are appropriate for endocytosis by the target cells, eg. dextran-coated spinels less than 500 angstroms in size (including the dextran coat). This helps assure the flow characteristics of the particles through the remainder of the synthesis and results in the production of only 100–500 angstrom particles which have a number of physiological advantages.

Finally, where a targeting moiety is used, when all these measures are taken, it is possible to take advantage of the versatility and convenience of reusable agarose based affinity chromatography media to remove all particles which are not bound to a targeting moiety as well as permitting the discard of all particles whose bound targeting moiety has been inactivated or otherwise lost its specificity during the synthetic process. The potential to use these media is quite important since this permits the preparation of affinity media with a wide variety of ligands which can be used to purify a correspondingly wide variety of targeted particles.

The final result is an agent with very nearly one active targeting moiety per particle with all particles selectively active and small enough for effective use. This can then be concentrated or formulated as desired and filter sterilized in small volume if necessary. The final sterilization can be with conventional 0.2 micron filters for bacterial clearance or with 0.1 micron filters to assure removal of small mycobacterial contaminants.

An alternative method of obtaining high specific activity is to actually coat all of the particles in the preparation with a large number of molecules of the targeting moiety. This has the undersirable effects of greatly increasing the expense of the product when the targeting moiety is expensive to produce, increasing the antigenicity of the particle, and in many cases, altering the distribution of the particle in undesirable ways. It is well known from work in affinity chromatography on solid supports that spacing and density of affinity ligands are crucial determinants of efficacy.

There has been considerable interest in the medical uses of various types of particulate therapeutic or diagnostic agents.

Thus Widder (U.S. Pat. No. 4,849,210) and Jacobsen (U.S. Pat. No. 4,863,715) demonstrated the effectiveness of suspensions of ferromagnetic particles as intravenous MRI contrast agents with various methods of synthesis. Groman (U.S. Pat. No. 4,827,945) provided a number of additional methods of synthesis of superparamagnetic particles and suggested the MR intravascular use of a wide range of labelled particles analogous to those disclosed for in vitro use by Molday. Although the compounds they describe are physically very similar to those disclosed by Molday (U.S. Pat. No. 4,452,773) they discuss sterilization techniques and methods of use involving diagnostic MRI. However, the particles produced by the methods of Groman vary in size from 100 to 5,000 Angstroms, cannot be filter sterilized in concentrated final form, and cannot be effectively purified by affinity chromatography since, like the compounds of Molday, they contain many constituents which will not pass readily through agarose based affinity media late in the preparation. Because of the need for autoclaving of the Groman products, the use of delicate protein ligands is severely limited because they cannot withstand autoclaving. It is possible to carry out the synthesis of Groman using ultraclean facilities so that final sterilization of the product is less important but this adds considerably to the expense of manufacture Other types of particulate agent have also generated much interest, eg. microspheres and nanospheres. The composition of such particles include latex polymers from various methacrylates, polylactic acid, protein/albumin, lipids and various other materials (see for example Proc. Soc. Exp. Biol. Med 58: 141–146 (1978), AJR 149: 839–843 (1987), J. Cell Biol. 64: 75–88 (1975), J. Microencaps 5: 147–157 (1988), Ann NY Acad Sci 507: 141–154 (1987), Ann NY Acad Sci 507: 120–140 (1987), Ann NY Acad Sci 507: 104–119 (1987) and Radiol. 163: 255–258 (1987)). These particles have been used as organic drug delivery systems, imaging agents, and for histological studies of axonal transport. They offer unique patterns of metabolism and biodistribution and continue to be the subject of intense investigation by many groups. The use of such particles for in vivo diagnostic imaging of axonal transport or as part of a drug delivery system that employs an intraneural route and axonal transport is also described in PCT/EP91/01780. The disclosures of these and the other publications and patent applications referred to herein are incorporated herein by reference.

The particles used according to the invention preferably comprise therapeutically or prophylactically loaded and optionally diagnostically marked inorganic crystals, e.g. radionuclide containing metal oxides. It will be recalled that in the methods of the invention where the particles carry specific targetting moieties radionuclides may perform a dual role: as cytotoxic agents to kill off infected cells which endocytose the particles, and as diagnostic markers to enable particle distribution, and by implication disease distribution, to be detected and possibly imaged. Suitable radionuclides include a number of nuclides emitting positron and electron β-particles all of which can be included in metal oxides, eg. spinels such as ferrites, either as substituents i the crystal lattice or as seeds, eg. $ZrO_2$, inside ferrite spinel shells. In one set of embodiments, the positron emitting isotopes of manganese ($_{25}Mn^{52}$), iron ($_{26}Fe^{52}$) cobalt ($_{27}Co^{55}$), or rhodium ($_{45}Rh^{99}$) are used in the synthesis of spinel particles, eg. sub-domain sized ferrite particles. The inclusion of cobalt or manganese in this type of ferrite has previously been difficult to achieve efficiently, but it is possible to reliably introduce cobalt, manganese, or other metals in amounts up to ⅓ of the number of metal atoms per formula unit, e.g. with the remaining ⅔ being Fe(III) if the stoichiometry of the desired crystal structure, e.g. garnet or spinel, is carefully considered and factors such as pH, temperature, and precursor metal salt and coating compound concentrations and the duration of heat incubation after precipitation are carefully controlled, preferably after optimization by routine experimentation. Thus as an example, for dextran coated particles it has generally been found advantageous to precipitate out from a saturated dextran solution. Thus all the divalent metal atoms may be replaced as opposed to the ½ or fewer suggested by Groman in U.S. Pat. No. 4,827,945.

These particles may be synthesized in such a way that they are stably coated with dextran or other hydrophilic molecules and the coating may then if desired be activated and bound covalently to antibodies or any type of cell adhesion molecule which will promote uptake of the particles by the cells which are to be treated according to the method of the invention. Particles so fashioned will be detectable upon Positron Emission Tomography (PET) as positron sources, and also upon Magnetic Resonance Imaging (MRI) as superparamagnetic particles. Some of these will also be detectable upon Magnetic Resonance Spectroscopy (MRS) as high receptivity nuclei at selected frequencies or on X-ray CT scanning where the Z-number and particle concentration is sufficient.

In positron ferrites made with $_{25}Mn^{52}$ the emission detection is based on the 0.511 MeV annihilation photons due to positron decay ($\beta$+27.9%, 0.575 MeV, E.C. 72.1%) with a half life of 5.59 days and associated gamma emissions of (100%, 1.434 MeV; 94.5%, 0.935 MeV; 90%, 0.744 MeV; 5%, 1.33 MeV; 4%, 1.25 MeV; 3%, 0.85 MeV) to $_{24}Cr^{52}$ which is stable. This is a decay half life which is quite well suited to long nerve transports and to full monoclonal antibody distribution for tumour studies and to the assessment of particle distribution among the various populations of CD4 positive cells. Further, with a relatively low positron energy of just 0.575 MeV, the spatial resolution is substantially better than any positron emitter in active clinical use including $_9F^{18}$. The high gamma emission may make $_{25}Mn^{52}$ less attractive for clinical use in some situations, but there are many alternatives.

Positron ferrites can also be made with $_{26}Fe^{52}$ which undergoes positron decay ($\beta$+56%, 0.804 MeV; EC 43.5%) with a half life of 8.275 hours and associated gamma emissions (99.2%, 0.169 MeV) to $_{25}Mn^{52}$ which is metastable and decays with a half life of 21.1 minutes by positron decay ($\beta$+96.27%, 2.631 MeV; EC 1.53%) and associated gamma emission (97.8%, 1.434 MeV) to stable $_{24}Cr^{52}$ as well as by isomeric internal conversion (2.2%, 0.378 MeV) to $_{25}Mn^{52}$.

This type of positron ferrite has the advantage of a strong positron emission signal during the day of injection with a fairly rapid decline towards the continuing positron emission of the $_{25}Mn^{52}$ with a 5.7 day half life.

An intermediate half life can be provided by positron ferrites made with $_{27}Co^{55}$ which undergoes positron decay ($\beta$+77%, 1.54 MeV; EC 23%) with a half life of 17.5 hours and associated gamma emissions (75%, 0.93 MeV; 16.5%, 1.41 MeV; 20.3%, 0.477 MeV; 7%, 1.32 MeV; 1.37 MeV) to $_{26}Fe^{55}$. This nuclide of iron then decays slowly by K-shell electron capture (0.006 MeV) with a half life of 2.7 years to $_{25}Mn^{55}$ which is stable.

Although the half life of this cobalt positron emitter may be useful in some cases, its use is inhibited by the decay pattern of $_{26}Fe^{55}$; the energy of the photon is quite low, but the irradiation continues for a long time and virtually all the energy is deposited within tissue as non-penetrating radiation.

A fourth type of positron ferrite can be synthesized with $_{45}Rh^{99}$ which undergoes positron decay (1.03 MeV) with a half-life of 16.0 days and no associated gamma emission to $_{44}Ru^{99}$ which is stable. This however is a longer half life than will generally be needed.

The decay for $_{21}Sc^{43}$ ($\beta$+78%, 1.22 MeV; EC 22%) and associated gamma emission (22%, 0.373 MeV) with half life of 3.9 hours to stable $_{20}Ca^{43}$ make this very promising. The substantial increase in ionic radius and the tendency to change from trivalence to divalence upon transition from Sc to Ca will be disruptive to the spinel crystal, but this may aid in the more rapid metabolism of the particles and thus the more rapid release within the targeted cell of the therapeutically or prophylactically effective element with which the particle is loaded.

Except for calcium, all of these nuclides are accommodated in the spinel ferrite crystal, although the chromium decay products from $_{25}Mn^{52}$ and $_{26}Fe^{52}$ will generate some regions of spinel chromite ($FeCr_2O_4$) within the inverse spinel ferrite ($Mt[II]O:Fe[III]_2O_3$) crystal. Similarly, some regions of ilmenite, perovskite, and titanium spinel will form in consequence of eg. $_{23}V^{48}$ decay.

The optimal method for producing $_{26}Fe^{52}$ with minimal $_{26}Fe^{55}$ contamination is by the irradiation of $_{24}Cr^{50}$ enriched chromium with cyclotron generated 38 MeV $_2He^4$ beams ($_{24}Cr^{50}(\alpha,2n)_{26}Fe^{52}$) with subsequent acid extraction, oxidation, evaporative drying, ether phase separation, redrying and filtration for sterilization (see Zweit Int. J. Radiat. Appl. Instrum. Part A, Appl. Radiat, Isol 39: 1197–1201 (1988)). Other reactions available for the production of $_{26}Fe^{52}$ include $_{25}Mn^{55}$ (p,4n)$_{26}Fe^{52}$, $_{24}Cr^{nat}(\alpha,xn)_{26}Fe^{52}$, $_{24}Cr^{nat}(_2He^3, xn)_{26}Fe^{52}$, $_{28}Ni^{nat}(p, spall)_{26}Fe^{52}$ with subsequent acid extraction and purification by anion exchange chromatography, wherein $_{24}Cr^{nat}$ includes $_{24}Cr^{50}$ (4.35%), $_{24}Cr^{52}$ (83.79%), $_{24}Cr^{53}$ (9.50%), and $_{24}Cr^{54}$ (2.36%).

$_{25}Mn^{52}$ may also be synthesized by standard techniques including $_2He^3$ activation of Vanadium $_{23}V^{51}(_2He^3, 2n)_{25}Mn^{52}$ (see Sastri Int. J. Appl. Rad. Isol. 32: 246–247 (1981)) or other cylcotron reactions including $_{24}Cr^{52}(p, n)_{25}Mn^{52}$, $_{24}Cr^{52}(d,2n)_{25}Mn^{52}$. Methods for $_{27}Co^{55}$ include $_{26}Fe^{54}(d,n)_{27}Co^{55}$, $_{26}Fe^{56}(p,2n)_{27}Co^{55}$, $_{26}Fe^{nat}(_2He^3, xnp)_{27}Co^{55}$, $_{25}Mn^{55}(_2He^3, 3n)_{27}Co^{55}$, $_{25}Mn^{55}(\alpha,4n)_{27}Co^{55}$, wherein $_{26}Fe^{nat}$ is composed of $_{26}Fe^{54}$(5.82%), $_{26}Fe^{56}$(91.8%), $_{26}Fe^{57}$(2.1%), and $_{26}Fe^{58}$(0.28%).

Generator techniques in which a longer half-life parent nuclide is synthesized and transported to the clinical site with subsequent extraction of the clinically useful daughter nuclide just prior to use can be arranged for several useful metals. These include $_{46}Pd^{100}$ (4.0d K,$\gamma$)$\rightarrow _{45}Rh^{100}$ (20h $\beta$+), $_{74}W^{188}$ (69d $\beta$–: 188m, 18m $\gamma$) $\rightarrow _{75}Re^{188}$ (16.7h $\beta$–), and $_{76}Os^{194}$ (6.0y $\beta$–)$\rightarrow _{77}Ir^{194}$ (17.4h $\beta$–).

A proposed cyclotron $_{21}Sc^{43}$ synthesis involves the following scheme which would apply for alpha particle bombardment of $_{20}Ca^{40}$ (thermal neutron cross section=0.43 barns):

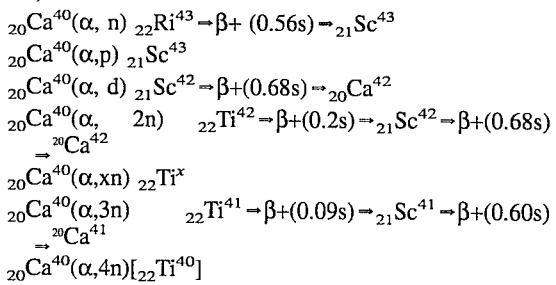

The calcium and scandium are readily separated either by phase separation (see Hara in Int. J. Appl. Rad. 24: 373–376 (1973)) or by chromatography (see Kuroda in J. Chrom 22: 143–148 (1966)) which also permits separation of any titanium.

These and other transition metal or lanthanide nuclides can be used in the synthesis of radioactive metal compounds (e.g. a metal oxide, metal sulphide or alloy, such as a ferrite) for use in monoclonal antibody based treatment of tumours by irradiation. Here again, the biodistribution and clearance of the delivered radionuclides is quite different from single atoms chelated to the proteins. Intravascular injection of $Fe^{59}$ labelled particles of the type described demonstrated a biphasic plasma half-life with about ¾ of the dose being cleared to spleen, liver, marrow, and slightly to lung over 1–2 hours, but with a substantial fraction of the dose demonstrating a quite prolonged plasma half life of many hours. Each antibody molecule can be used to deliver several hundred or several thousand atoms of the desired nuclide so achieving a high local dose. It should also be noted that binding multiple emitter atoms to a single protein molecule has been known to rapidly destroy the protein—this problem is substantially alleviated by the particles according to the invention because the emitting nuclei are for example up to 100 angstroms distant from the targeting moiety—thus the chance of any electron, positron, or gamma-ray interacting with the targeting moiety is reduced by several orders of magnitude. Methods developed for antibody delivery of $_{39}Y^{90}$ can be applied with a far higher concentration of this nuclide included in a conjugated ferrite.

Magnetic properties of the particles can also be used to help control delivery.

Turning now to PET image resolution, one of the limitations on scanning resolution is a result of the distance travelled by the positron after the decay event but before electron-positron annihilation. This distance is dependent upon the energy of the characteristic β emission for a given nuclide. The maximum range for an $_9F^{18}$ positron emitted at 0.64 MeV is 2.6 mm while the particles from $_{37}Rb^{82}$ decay emitted at 3.35 MeV travel up to 16.5 mm before annihilation. Along this path, the positron loses energy by interacting with the electrons of atoms it passes, causing a variety of ionizations and excitations. Only when most of the kinetic energy is expended does the positron interact with an electron in a matter-antimatter annihilation reaction generating two 0.511 MeV photons travelling approximately 180° away from each other. The residual momentum of the positron at the time of the annihilation imparts some translational momentum to the emitted photons resulting in an angle between the two which differs from 180°. Measurements of this angle reflect the nuclide and the medium in which the energy losses and subsequent annihilation take place.

It has been known for some time that the distance of travel of the positron prior to annihilation is proportional to the density of the medium. The density of magnetite is 5,180 kg/m$^3$, just over five times greater than most animal tissues and, according to classical calculations based on electron range measurements, this potentially results in an 80% decrease in the maximum distance travelled by a positron travelling in magnetite as opposed to travelling in tissue. There is an increase in Brehmsstrahlung braking radiation proportional to the effective Z number of magnetite (which= 52), but this only accounts for 1% of energy loss for a population of positrons.

The numbers stated above for travel of the positron before annihilation reflect maxima. In fact during positron emission, the decay energy is divided between the positron and a neutrino and the division is variable, thus resulting in a population of energies. The mean energy of a positron from a given nuclide is about ⅓ of the maximum usually given as the particle energy. The means positron energy from $_{25}Mn^{52}$ is 0.19 MeV and in magnetite this classically would result in a range of about 20 microns if the travel were entirely in magnetite.

However various elements have characteristic positron affinities and these have profound impact on positron lifetimes. Therefore, the classical view of positron range in relation to a general density measurement proves to be a substantial oversimplification.

It can therefore be seen that by using high affinity nuclides such as lithium in the β-emitter loaded particles, the positron range can be further decreased.

In addition, it has been learned that defects in a crystal can cause trapping of positrons. Defects in $YBaCuO_x$ perovskite crystals are particularly effective at positron trapping even when these materials are not in a superconducting state, however, even mechanical stress defects in metals are fairly effective. There are also effects due to the magnetic field generated by a moving positron and its interaction with the spontaneous field of a material such as magnetite, as well as electron interaction enhancement effects due to the number of unpaired, anti-spin matched electrons from d or f orbitals in the particular spinel used for the particulate shield.

The consequence of these considerations is that it is possible to begin with a crystal seed of a positron emitting nuclide including several thousands atoms of the emitter and then to precipitate a lithium or zinc doped, defected, magnetite shield around the positron emitting core. This shield will cause a very large fraction of the emitted positrons to undergo all of their ionization producing collisional losses within the particle and therefore to annihilate without ever leaving the particle. Those positrons that do emerge from the surface of the particle without being affected by reflection or surface trapping effects will have a greatly reduced energy distribution, travel far shorter distances through tissue, and create far fewer ionizations in tissue per decay event than standard unshielded positron emitters.

The annihilation photons themselves are relatively unaffected by the presence of ferrite as opposed to tissue in their surroundings. Therefore, there will be a very large decrease in tissue ionizations with only a trivial decrease in photon emissions. Further, the photon emissions will all take place far closer to the location of the actual tracer atom, typically within several microns rather than within millimetres and this will result in an improvement in the spatial resolution of the PET scan. Further, the annihilations, as a population, will have lower momentum and this will shift the population annihilation angle closer to 180°, further improving the resolution of the scan.

This shielding effect can thus be used to achieve extremely limited ranges of cytotoxic ionization injury. An example of a use for such an ultra-short range β emitting particle would be in the treatment of AIDS. Here, a particle with antibodies or other adhesion molecules targeted to infected CD4+ macrophages, monocytes, and T-cells would be used to cause selective endocytosis of the particles. Larger particles are cleared from the blood stream over 1–2 hours by monocytes and fixed RES cells in lymph nodes, spleen, liver and lung, but coinjection with cold-indifferent antibody particles allows selective uptake of β-emitting particles targeted to gp-120 antigens (such as the CD4 binding site) detectable on the cell surface of infected CD4 cells. The β-emitting particles provide the cytotoxcity which the compromised patient is unable to provide. Killing of infected monocytes will prevent their excessive uptake of circulating IL-2, prevent their contact infection of approaching T-cells, and prevent them undergoing destructive syncytial fusion with uninfected macrophages. The range of the emitted β-radiation can be designed to be not much greater than the size of a single target cell, thus limiting effective irradiation to only those cells that actually ingest the particle and taking advantage of the terminal Bragg peak effect which increases the ionization rate for a low energy positron just before annihilation. A short half life emitter could be used to minimize the effect of increasing exposure range with digestion of the coating (which may take days) and multiple treatments could then be carried out. Larger particles can be used without magnetic aggregation by composing the shell of less magnetic nuclides.

The particles used according to the invention, e.g. mixed spinels, may be additionally be diagnostically marked to enable their distribution to be detailed using magnetic resonance spectroscopic tracing and heteronuclear imaging methods. When large percentages of $_3$Li, $_{21}$Sc, $_{27}$Co, $_{25}$Mn, $_{29}$Cu, $_{59}$Pr, $_{71}$Lu, or $_{75}$Re are introduced into ferrite crystals these become vehicles for delivering large groups of those atoms to a desired site. These elements and their various isotopes have high nuclear resonant receptivity when in the appropriate oxidation state and electron/chemical environment and so the MR machine can be used as a spectrometer to detect the presence of these crystals. Any high receptivity metal in an oxidation state where electrons do not produce confounding relaxation (e.g. $Mn^{7+}$, $Co^{3+}$) or in which d-electron orbitals are entirely empty ($Sc^{3+}$) or full ($Zn^{2+}$) are particularly amenable. The chemical environment is also important to minimize the effects of quadrupolar relaxation for nuclei with $I>\frac{1}{2}$.

Nuclei such as $F^{19}$ and $In^{115}$, ie. markers for $F^{19}$ or $In^{115}$ MR imaging, can be included in compounds which can then be included or embedded in latex, protein, polylactic acid or other polymers and in the coating of metal compound particles with a targeting moiety also present in the coating.

Using particle types and delivery targeting systems as described above, a different group of metals can be used instead of the β-emitters to achieve the very short range radiotherapy effect. These are a variety of nuclides in which decay is by K-shell capture. Although decay in these nuclides involves collapse of an electron into the nucleus, the resulting vacancy causes effects among the remaining electrons which result in Auger and Coster-Kronig electron emissions. These have extremely low energies and resulting ranges of micron and submicron distances, although several such electrons may be emitted for each single decay event. An optimal nuclide with this behaviour for HIV therapy is $_{46}$Pd$^{103}$ which is a pure K-capture nuclide with a 17 day half life; $_{24}$Cr$^{51}$ may also advantageously be used.

The particles used generally should be metal compounds capable of precipitation to a stable colloid having a particle size suitable for cell uptake and preferably having a surface capable of being coated with or bound to biochemically useful materials, e.g. carbohydrates or proteins.

The particles useful in the methods according to the invention may be produced by relatively straightforward methods—forming particles of a matrix material comprising the therapeutically or prophylactically active element and optionally a diagnostic marker, for example by precipitation, e.g. from an appropriately buffered solution; optionally separating out therefrom particles of a desired size range; optionally coating said particles with a physiologically tolerable optionally biodegradable coating material, e.g. a natural or synthetic polymer or derivative thereof such as latex, polylactic acid, proteins, albumin, polysaccharides, starches, dextrans, polymerized sugar alcohols, etc (see for example EP-A-184899 (Jacobsen)); and optionally conjugating said particle (optionally via coupling to a said coating, optionally after appropriate derivatization thereof e.g. to provide a binding site or to block excess binding sites) to a cell adhesion molecule, preferably with a CAM: particle ratio of up to 10, especially up to 5 more especially up to 2 and most preferably about 1; optionally separating CAM-conjugated particles so formed from unconjugated particles, preferably by size separation, especially preferably by repeated size separation followed by at least one affinity separation; optionally sterilising the CAM-conjugated particles, if desired after formulation thereof with a pharmaceutical carrier and optionally with further conventional pharmaceutical excipients, e.g. viscosity enhancing agents, pH regulators, osmolality adjusting agents, etc.

As discussed above, the matrix material used may be an inorganic matrix, e.g. a metal oxide, or an organic matrix, e.g. a polymer such as a cross-linked starch or dextran, which will serve as a carrier for the therapeutically or prophylactically active element or diagnostic marker.

Incorporation of the active element or marker within a carrier matrix can be achieved by conventional techniques, for example by co-precipitation, by steeping a porous matrix material to impregnate it with the desired agent or marker, by exposing the agent to ultrasonically suspended, uncoated metal oxide particles, or by means of the buffered precipitation technique described herein.

The matrix particles should desirably be relatively uniformly dimensioned, e.g. within the ranges discussed above, and this may be achieved for example by conventional screening or particle precipitation techniques. Monodisperse particles will be preferred.

Viewed from a further aspect the invention provides a process for the preparation of a particulate pharmaceutical agent according to the invention which process comprises admixing endocytosable particles comprising a therapeutically or prophylactically active element with at least one pharmaceutical carrier or excipient.

Viewed from a yet still further aspect the invention also provides a process for the preparation of the modified spinel, garnet and perovskite particles according to the invention which process comprises precipitating di and trivalent metal ions of ionic radii such as to permit crystals of spinel, garnet or perovskite structure to form, said precipitation being from a solution containing an element having a desired therapeutic or prophylactic activity, especially palladium, and optionally also containing a further element selected to modify the crystal structure of the precipitated crystals to permit particle size control and to adjust the rate of post-phagocytosis intracellular breakdown of the particles; and optionally conjugating resulting particles, optionally after size separation and coating, with a cell adhesion molecule, preferably gp120.

In the particle precipitation processes according to the invention the active elements or markers to be incorporated into the particles may themselves be in solution or alternatively they may be in fine "seed" crystals which become included in the precipitating particles.

For administration in vivo, the dosages used will clearly depend upon a wide range of factors such as the patient's weight, the specificity of the TM or CAM (for TM or CAM-conjugated agents), the nature of the active element or diagnostic marker component of the pharmaceutical agent, the nature extent or severity of the disease that is being treated, etc. The appropriate dosage however can readily be determined taking these factors into account. Generally doses may be expected to be of the order of 50 micromoles of therapeutic cation per kg bodyweight.

Endocytosable particles may also be used generally as a research tool for investigation of cell function where the particles are such as to release within the cell cations that can be detected externally, e.g. due to their radioactive decay or nuclear magnetic resonance characteristics. Thus they may be used to substitute externally detectable cations for undetectable physiological cations in intact cells and in targetted groups of cells in intact animals in order to mark metal binding proteins and other biomolecules to study cation metabolism and other activities of such proteins and biomolecules. Viewed from this aspect the invention provides a composition comprising particles capable of being endocytosed and of subsequent intracellular release of metal cations which compete with cations native to the endocytosing cells and which are detectable from outside the cells.

The palladium containing iron oxide particles useful according to the invention are themselves novel and viewed from a still further aspect the invention provides a crystalline material comprising palladium disposed within an iron oxide matrix.

The invention is illustrated in more detail by the following Example.

EXAMPLE

Ferrite particle synthesis can be efficiently carried out in less than 24 hours. The chloride salts of the of 2+ and 3+ oxidation state metals, eg. $FeCl_2$, $FeCl_2$, $MtCl_2$, $MtCl_3$ where Mt is a therapeutically or prophylactically active metal or a diagnostic marker are dissolved in a saturated or supersaturated solution of 1,500 to 10,000 MW dextran, preferably 10,000 MW in a ratio near Mt(II)1.0:Fe(III) 2.0 at a concentration of 0.2 to 1.0 molar, and at a temperature of 0°–60° C. depending upon the final particle size distribution desired but preferably at 50° C. and where Mt is the divalent cation of a transition metal or of a mix of transition metals. Typical starting amounts are 540 mg $FeC_3$, 230 mg $FeCl_2$, 3 gm Dextran 10 K, in 4.5 ml of $dH_2O$. The dextran solution should be heated only briefly to avoid recrystalization or sludging. (It should be noted however that for palladium ferrites, dextran coating in this fashion is not required for particle phagocytosis and subsequent intracellular palladium release.)

Trivalent cations (such as Sc(III)) may be used in low ratios if they are stoichiometrically balanced with monovalent metal salts, preferably LiCl. The ferrites are precipitated by addition of 5 to 10%, preferably 7.5% aqueous solution of $NH_3$ to reach a pH of 9 to 12 and preferably pH 11 (about 15 ml added to 7.5 ml of dextran/metal salt solution). This solution can be heated to 60° C. prior to adding it to the metal/dextran solution.

A variety of sizes of dextrans can be used, for example ranging from 1.5 K to 40 K MW although the 10 K dextrans have proven most reliable in these syntheses. Changes in outer coating also effect the tumbling behaviour of the particles and this can have an effect on some resonant behaviour of the particles and on their interactions with water molecules. It is also possible to coat the particles with non-metabolizing latex from for example cyanoacrylate monomers to alter their rate of processing through the cells. Other biodegradable coatings such as polylactic acid or even protein/albumin coats can be applied. A shift in average crystal core size towards smaller size can be produced by lowering the temperature of the synthetic reaction or elevating the pH. However, a variety of separation techniques may then be required to trim the size distribution to select the desired size range.

Additionally, the spinel crystal can be constituted of mixed metals in various amounts in order to achieve various specific optimizations. Mixed spinels including various useful transition series metals, and even some lanthanide metals can be made by adding the metal chloride directly to the saturated dextran solution prior to alkali precipitation.

The product of the reaction is centrifuged 2 times at 1,000 g×10 minutes and one time at 1,500 g×10 minutes to remove particulates which are discarded in the precipitate. The resulting suspension is passed through a 2.5 cm×40 cm column of Sephadex G-25M/150 ® (Pharmacia) equilibrated in 0.1 M NaAcetate buffer pH6.5 in order to remove free metal ions, particulates, ferrous hydrous oxides, chloride and ammonia.

The Sephadex eluant is then passed through successively finer microfilters. Two passes through a 0.22 micron nylon filter are followed by two passes through a 0.1 micron nylon filter. The third filtration is slow but can be accomplished with 100 mm or 47 mm diameter filters on a suction funnel using a 50 nm filter such as Millipore ®VMWP-04700 Cellulose MF filters although nylon or polycarbonate filters are preferable. The speed and general success of this step are highly dependent on the initial precipitation conditions—being most efficacious with smaller particle size distribution. (It should be noted that the ionic content of the water and the precipitation medium and the manner of preparation and purification of the dextran used can also affect particle size distribution). These filtrations may also be accomplished with centrifugal filters.

This is cleared, desalted, and size trimmed product is then concentrated with a Centriprep-30 ® (Amicon) ultrafilter, at 1,500 g for 45 minutes, to achieve a final volume of five to seven ml. The sample is then applied to a 2.5 cm×25 cm column of Sephacryl-200 ® (Pharmacia) equilibrated with 0.1 M NaAcetate buffer pH6.5 with elution by the same buffer. This traps dextran and small ferrous hydrous oxides while letting the particles pass in the excluded, unfractionated volume. The late tail of this fraction should be discarded as it contains much of the hydrous oxide. The resulting eluant is concentrated to 4 ml with a Centriprep-30 concentrator (1,500 g for 15 minutes) for conjugation.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through two PD-10 Sephadex G-25M/150 columns equilibrated with 20 mM NaBorate buffer pH8.5, concentrating with a Centriprep-30 ultrafilter to 1–2 ml then passing the sample through a third PD-10 column of Sephadex G-25M/150 to completely remove any unreacted periodate. The final volume is brought up to 4 ml with borate buffer.

A protein solution is prepared having 2–10 mg of antibody, lectin, growth factor, or other selective cell adhesion molecule dissolved in 1 ml of 20 mM NaBorate buffer, pH8.5. Where possible, blocking molecules to protect the active/recognition site should be added at this point if the blocker will not be bound by the periodate activated dextran. For example, adding 1 mM $CaCl_2/MnCl_2$ helps protect the binding site on some lectins. This solution is then added to the particle solution, mixed, and allowed to incubate for 4 to 12 hours depending upon the molecule involved and the number of adhesion molecules desired per particle. The reaction is quenched by the addition of 200 microliters of 0.5 M glycine with an additional two hours of incubation.

The covalent bonds are then reduced by the addition of 0.5 ml of 0.25 M $NaBH_4$ with allowance for the generation of $H_2$ gas. After one hour of reaction, the mixture is passed through three PD-10 columns of Sephadex G-25M/150 equilibrated with 20 mM HEPES buffer at a pH of 7.4 to remove glycine, $NaBH_4$ and $H_2$, then concentrated to a 1–2 ml volume with a Centriprep-100 concentrator (500 g for 60 minutes) to clear unbound adhesion molecule and smaller, unconjugated particles. This product is then applied to a 1.6×35 cm column of Sephacryl 200 and eluted with 20 mM HEPES buffer at pH 7.4. This column run further removes unbound targeting molecules and traps any newly formed hydrous oxides. The eluant is collected and concentrated with a Centriprep-100 concentrator at 500 g×30 minutes to achieve a final volume of 4 ml.

The four ml of reaction product are then applied to a 4 ml column of affinity ligand Sepharose 6B with divinyl sulfone links (such as Sigma A2278 for some lectins) equilibrated with 20 mM HEPES buffer pH 7.4. It is preferable to avoid conditions normally intended to maximize binding as this may make it impossible to elute the specific fraction. The column is then washed extensively with four to five volumes of buffer and then a 2 ml volume of 1 molar affinity eluant in the same buffer is applied. This elutes the active fraction in a fairly sharp band.

The specific fraction is collected and passes through a PD-10 Sephadex G-25M/150 column to help clear affinity eluant and then concentrated to 1 mL with a small volume Centricon-30 centrifugal concentrator (1,500 g×20 minutes). This product is passed through a second PD-10 column and the final output then concentrated to a volume of 300 to 500 microliters with a Centricon-30 concentrator (1,500 g×60 minutes). The final product is then sterilized by 0.22 or 0.1 micron filtration using a Costar 1 ml centrifugal microfilter and stored for use.

The ferrite particles can be obtained by similar procedures, e.g.:

(a) The ferrite particles are synthesized by a modification of the method of Molday (J. Immunol. Meth. 52:353–367 (1982)) which can be efficiently carried out in less than 24 hours. The chloride salts of the metals with the positron nuclide at specific activities of 10–100 mCi/μM (370 MBq-3.7 GBq/μM) of 2+ oxidation state metal are dissolved in a supersaturated solution of 10,000 MW dextran in a ratio near Mt(II)1.0:Fe(III) 2.0 at a concentration of 0.5:1.0 molar and at a temperature of 20°–60° C. depending upon the final particle size distribution desired and the ferrites are precipitated by addition of 8% aqueous solution of $NH_3$ to reach a pH of 11 (about 4 ml added to 2 ml of dextran/metal salt solution), centrifuged at 1,000 g to remove particulates, separated and concentrated with a Centriprep-30 (Amicon) concentrator at 2,000 g for collection of small particles in the filtrate when desired.

The products of this concentration/separation step, either filtrate (reconcentrated with Centriprep-10 concentrator) or retentate, are passed through a preparative column of Sephadex G-25M (150) equilibrated in 0.1 M NaAcetate buffer pH6.5 at least four times the volume of the applied sample in order to remove free metal ions, chloride and ammonia.

This desalted sample is again concentrated with a Centriprep-30 concentrator (2,500 g for one hour) to a 3 ml volume then passed through a 2.5 cm×25 cm column of Sephacryl-300 (Pharmacia) equilibrated with 0.1 M NaAcetate buffer pH6.5 with elution by 0.1 M NaAcetate/0.15 M NaCl buffer pH6.5 and 0.15 M NaCl to separate unbound dextran, and the resulting fraction concentrated to 4 ml with a Centriprep-30 concentrator (2,500 g for 15 minutes) and activated by reacting with 1 ml of 20 mM $NaIO_4$ at 23° C. while stirring (non-magnetic stirring only) for 60 minutes in the dark.

The periodation reaction is halted by passing the ferrite sample through a Sephadex G-25M (150) column equilibrated with 20 mM NaBorate buffer pH8.5, concentrating with Centriprep-30 to 1–2 ml then passing the sample through a second column of Sephadex G-25M(150) to completely remove any unreacted periodate. The protein solution of 2–10 mg of antibody, lectin, growth factor, or other selective cell adhesion molecule dissolved in 1 ml of 20 mM NaBorate buffer pH8.5 is then added to the ferrite solution, mixed, and allowed to incubate for 4 to 12 hours depending upon the molecule involved and the number of adhesion molecules desired per ferrite particle. The reaction is quenched by the addition of 200 microliters of 0.5 M glycine with additional two hours of incubation.

The covalent bonds are then reduced by the addition of 0.5 ml of 0.25 M $NaBH_4$ with allowance for the generation of $H_2$ gas. After one hour of reaction, the mixture is passed through a column of Sephadex G-25M(150) equilibrated with 20 mM HEPES buffer at a pH of 7.4 to remove $NaBH_4$ and $H_2$, concentrated to a 1–2 ml volume with a Centriprep-30 concentrator (2,500 g for 30 minutes) and applied to a 1.5 cm×40 cm column of Sephacryl-300 equilibrated with 20 mM HEPES buffer pH7.4 for subsequent elution with 20 mM HEPES/0.15 M NaCl buffer pH7.4 in order to remove unbound adhesion molecules and passaged into 0.1 M phosphate buffer pH7.4 via Sephadex G-25M for administration.

The resulting fraction can then be concentrated to a 1 ml volume with a Centriprep-30 concentrator for use or further purified with affinity chromatography and subsequent concentration when necessary. Reconstitution after freeze drying can also be used if desired.

The product of the precipitation reaction may alternatively be centrifuged 3 times at 1,000 g to remove particulates which are discarded in the precipitate. The resulting suspension is passed through a preparative column of Sephadex G-25M/150 ® (Pharmacia) equilibrated in 0.1 M NaAcetate buffer pH6.5 at least five times the volume of the applied sample in order to remove free metal ions, chloride and ammonia.

This cleared and desalted product may then be concentrated with a Centriprep-100 ® (Amicon) ultrafilter, at 1,500 g for two hours, resuspended and again concentrated to a 4 ml volume. This yields good clearance of particles below 5 nm and of unbound dextran into the filtrate for discard and this is a preferred method for the particulate agent.

When a range of particle sizes including smaller particles are to be processed, this concentration step is done with a Centriprep-30 concentrator. In this case, the unbound dextran will have to be removed by applying the sample as a 3–4 ml volume to a 2.5 cm×25 cm column of Sephacryl-200 ® (Pharmacia) equilibrated with 0.1 M NaAcetate buffer pH6.5 with elution by 0.1 M NaAcetate/0.15 M NaCl buffer pH6.5 and 0.15 M NaCl. The resulting fraction concentrated to 4 ml with a Centriprep-30 concentrator (2,500 g for 15 minutes) for conjugation.

When only very small particles are desired, the initial concentration is done with a Centriprep-100 ultrafilter, but it is the filtrate which is then processed further. This filtrate is reconcentrated three times with a Centriprep-30 ultrafilter to clear the dextran.

When primarily larger particles (in the 50 to 300 nm range) are desired, the desalted, ultrafiltered sample is concentrated with a Centriprep-100 concentrator (2,500 g for one hour) to a 4 ml volume and then applied to a 2.5 cm×25 cm column of Sephacryl-400 R (Pharmacia) equilibrated with 0.1 M NaAcetate buffer pH6.5 with elution by 0.1 M NaAcetate/0.15 M NaCl buffer pH6.5 and 0.15 M NaCl. The resulting fraction concentrated to 4 ml with a Centriprep-30 concentrator (2,500 g for 15 minutes) for conjugation.

For some uses it is preferable for the particles to be less than 50 nm in diameter. Therefore, the Centriprep 100 product may be passed through first 0.2 micron and then 0.1 micron Nalgene ® nylon microfilters. The resulting product is then concentrated to a 2 ml volume and applied to a 2.5 cm×50 cm column of Sephacryl-1000 ® (Pharmacia) for size fractionation. Particles in the later fractions are collected for further processing.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through a Sephadex G-25M (150) column equilibrated with 20 mM NaBorate buffer pH8.5, concentrating with a Centriprep-30 ultrafilter to 1–2 ml then passing the sample through a second column of Sephadex G-25M(150) to completely remove any unreacted periodate. The protein solution of 2–10 mg of antibody, lectin, growth factor, or other selective adhesion molecule dissolved in 1 ml of 20 mM NaBorate buffer pH8.5 is then added to the particle solution, mixed, and allowed to incubate for 4 to 12 hours depending upon the molecule involved and the number of adhesion molecules desired per particle. The reaction is quenched by the addition of 200 microliters of 0.5 M glycine with an additional two hours of incubation.

The covalent bonds are then reduced by the addition of 0.5 ml of 0.25 M $NaBH_4$ with allowance for the generation of $H_2$ gas. After one hour of reaction, the mixture is passed through a column of Sephadex G-25M(150) equilibrated with 20 mM HEPES buffer at a pH of 7.4 to remove $NaBH_4$ and $H_2$, concentrated to a 1–2 ml volume with a Centriprep-100 concentrator (1,500 g for 60 minutes) to clear unbound adhesion molecule and smaller, unconjugated particles. This product can then be passaged into 0.1 M phosphate buffer pH7.4 via Sephadex G-25M for administration, or further purified by affinity chromatography on non-porous beads or Nalgene ® affinity membranes.

The resulting fraction can then be diluted to 20 ml in sterile buffer and passed through a 0.2 micron or preferably 0.1 micron microfilter to assure sterilization. The final product is concentrated to a 1 ml volume with a Centriprep-100 concentrator for use. Reconstitution after freeze drying can also be used to achieve desired concentrations for some preparations.

Alternatively the product of the precipitation reaction is centrifuged 2 times at 1,000 g×10 minutes and one time at 1,500 g×10 minutes to remove particulates which are discarded in the precipitate. The resulting suspension is passed through a 2.5 cm×40 cm of Sephadex G-25M/150 ® (Pharmacia) equilibrated in 0.1 M NaAcetate buffer pH6.5 in order to remove free metal ions, particulates, ferrous hydrous oxides, chloride and ammonia. The Sephadex eluant is then passed through successively finer microfilters. Two passes through a 0.22 micron nylon filter are followed by two passes through a 0.2 micron nylon filter. The third filtration is slow but can be accomplished with 100 mm or 47 mm diameter filters on a suction funnel using a 50 nm filter such as Millipore ® VMWP-04700 Cellulose MF filters.

This cleared, desalted, and size trimmed product is then concentrated with a Centriprep-30 ® (Amicon) ultrafilter, at 1,500 g for 45 minutes, to achieve a final volume of five to seven ml. The sample is then applied to a 2.5 cm×25 cm column of Sephacryl-200 ® (Pharmacia) equilibrated with 0.1 M NaAcetate buffer pH6.5 with elution by the same buffer. This traps dextran and small ferrous hydrous oxides while letting the particles pass in the excluded, unfractionated volume. The late tail of this fraction should be discarded as it contains much of the hydrous oxide. The resulting eluant is concentrated to 4 ml with a Centriprep-30 concentrator (1,500 g for 15 minutes) for conjugation.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through two PD-10 Sephadex G-25M/150 columns equilibrated with 20 mM NaBorate buffer pH8.5, concentrating with a Centriprep-30 ultrafilter to 1–2 ml then passing the sample through a third PD-10 column of Sephadex G-25M/150 to completely remove any unreacted periodate. The final volume is brought up to 4 ml with borate buffer.

The protein solution of 2–10 mg of antibody, lectin, growth factor, or other selective cell adhesion molecule dissolved in 1 ml of 20 mM NaBorate buffer pH8.5. Where possible, blocking molecules to protect the active/recognition site should be added at this point if the blocker will not be bound by the periodate activated dextran. For example, adding 1 mM $CaCl_2/MnCl_2$ helps protect the binding site on some lectins. This solution is then added to the particle solution, mixed, and allowed to incubate for 4 to 12 hours depending upon the molecule involved and the number of adhesion molecules desired per particle. The reaction is quenched by the addition of 200 microliters of 0.5 M glycine with an additional two hours of incubation.

The covalent bonds are then reduced by the addition of 0.5 ml of 0.25 M $NaBH_4$ with allowance for the generation of $H_2$ gas. After one hour of reaction, the mixture is passed through three PD-10 columns of Sephadex G-125M/150 equilibrated with 20 mM HEPES buffer at a pH of 7.4 to remove glycine, $NaBH_4$ and $H_2$, then concentrated to a 1–2 ml volume with a Centriprep-100 concentrator (500 g for 60 minutes) to clear unbound adhesion molecule and smaller, unconjugated particles. This product is then applied to a 1.6×35 cm column of Sephacryl 200 and eluted with 20 mM HEPES buffer at pH 7.4. This column run further removes unbound targeting molecules and traps any newly formed hydrous oxides. The eluant is collected and concentrated with a Centriprep-100 concentrator at 500 g×30 minutes to achieve a final volume of 4 ml.

The four ml of reaction product are then applied to a 4 ml column of affinity ligand Sepharose 6B with divinyl sulfone links (such as Sigma A2278 for some lectins) equilibrated with 20 mM HEPES buffer pH7.4. It is preferable to avoid conditions normally intended to maximize binding as this may make it impossible to elute the specific fraction. The column is then washed extensively with four to five volumes of buffer and then a 2 ml volume of 1 molar affinity eluant in the same buffer is applied. This elutes the active fraction in a fairly sharp band.

The specific fraction is collected and passes through a PD-10 Sephadex G-25M/150 column to help clear affinity eluant and then concentrated to 1 ml with a small volume Centricon-30 centrifugal concentrator (1,500 g×20 minutes). This product is passed through a second PD-10 column and the final output then concentrated to a volume of 300 to 500 microliters with a Centricon-30 concentrator (1,500 g×60 minutes). The final product is then sterilized by 0.22 or 0.1 micron filtration using a Costar 1 ml centrifugal microfilter and stored for use.

(b) Coated particles and particularly ferrite particles have been prepared by a novel buffered precipitation technique.

This type of synthesis is particularly helpful when a coating is required which includes delicate molecules which cannot tolerate the strong alkaline conditions used in other precipitation methods. The chloride salts of the desired divalent and trivalent metals, preferably $Fe^{2+}$ and $Fe^{3+}$ but also including a variety of other transition and other metals are dissolved in $H_2O$ or in dextran/$H_2O$ solution or in a saturated dextran/$H_2O$ solution at a metal concentration of 0.2 to 1.0 molar as indicated by the dictates of stoichiometry and of the requirements of the particular application. Lower concentrations will tend to produce particle size distributions including generally smaller particles.

A precipitation bath is prepared as a strong buffer solution in $H_2O$, for example 1 molar HEPES or 1 molar Tris. When only iron chlorides are used, the pH of the solution may be as low as pH 6.0, although solutions at a pH of 7.4 are effective for many cations. When the intended coating molecule can tolerate higher pH, the buffer solution may be prepared at the highest tolerable pH, as for instance with many proteins which readily tolerate pH of 8.0 or 8.5.

The protein, pharmaceutical, targeting moiety, or other biomolecule is dissolved in the buffer solution at a concentration of 1 to 100 mg/ml or at higher or lower concentrations optimized for the expense of the agent and the efficiency of binding for a given type of molecule. The precipitation bath may also include bovine serum albumin, peptides, dextrans or other molecules which can help to coat the particles along with the pharmaceutically active agent. The bath is heated to 37° C. for many proteins, or may be used at ambient temperature, or at 0°–4° C., or at higher temperatures up to 60° C. as tolerated by the coating molecule of choice.

The metal chloride solution mixture is then brought to the chosen reaction temperature and added to the buffered precipitation/coating bath in dropwise fashion with continuous or intermittent mixing, preferably by a non-magnetic mixing technique. The ionic strength of the buffer bath will need to be two to ten times greater than the ionic strength of the metal solutions, preferably four to six times greater. This will limit the total volume as well as the total concentration of the metal solution, but in any case will result in the precipitation bath retaining its pH in the tolerable buffered range throughout the process of adding the metal solution.

For example, one ml of a solution of 0.33 M $PdCl_2$ and 0.66 M of $FeCl_3$ may be added to ten ml of a solution of HEPES pH 7.8 1 molar, with two mg per ml of CD4, possibly blocked with gp120 fragments to protect the binding site, and also 20 mg/ml of azidodideoxythymidine (AZT).

The precipitation mixture is incubated for 20 to 40 minutes at the reaction temperature, then centrifuged at 1,000 g three times for 10 minutes each and the supernatants saved while any precipitate is discarded. The particle solution is then passed through a column of Sephadex G-25M equilibrated in the final buffer of choice as for example in HEPES pH 7.4 200 mM where the volume of the column is five times the volume of the reaction product. The excluded fraction is collected then concentrated in Amicon Centriprep-30 ultrafilters at 1,500 g×45 minutes, diluted in buffer to 24 ml total, and then reconcentrated in Centriprep-100 ultrafilters to clear unbound coating molecules which are small than MW 100,000.

This concentrate may either be applied to an affinity column to selectively purify coated particles with active targeting moiety (e.g. on immobilized gp-120, or brought directly to filter sterilization in 200 nm centrifugal microfilters where no targeting moiety is used.

The efficacy of a range of different cationic cell therapy particles in the treatment of intracellular infection was demonstrated using as a model an assay of HIV-1 RT activity derived from the assay described by Potts (in "Techniques in HIV research", Ed Aldovini et al, Stockton, N.Y., 1990, pp 103–106) and also by demonstrating particle phagocytosis by target cells by electron micrography. These investigations are discussed below with reference to the accompanying drawings, in which:

Figure 7:
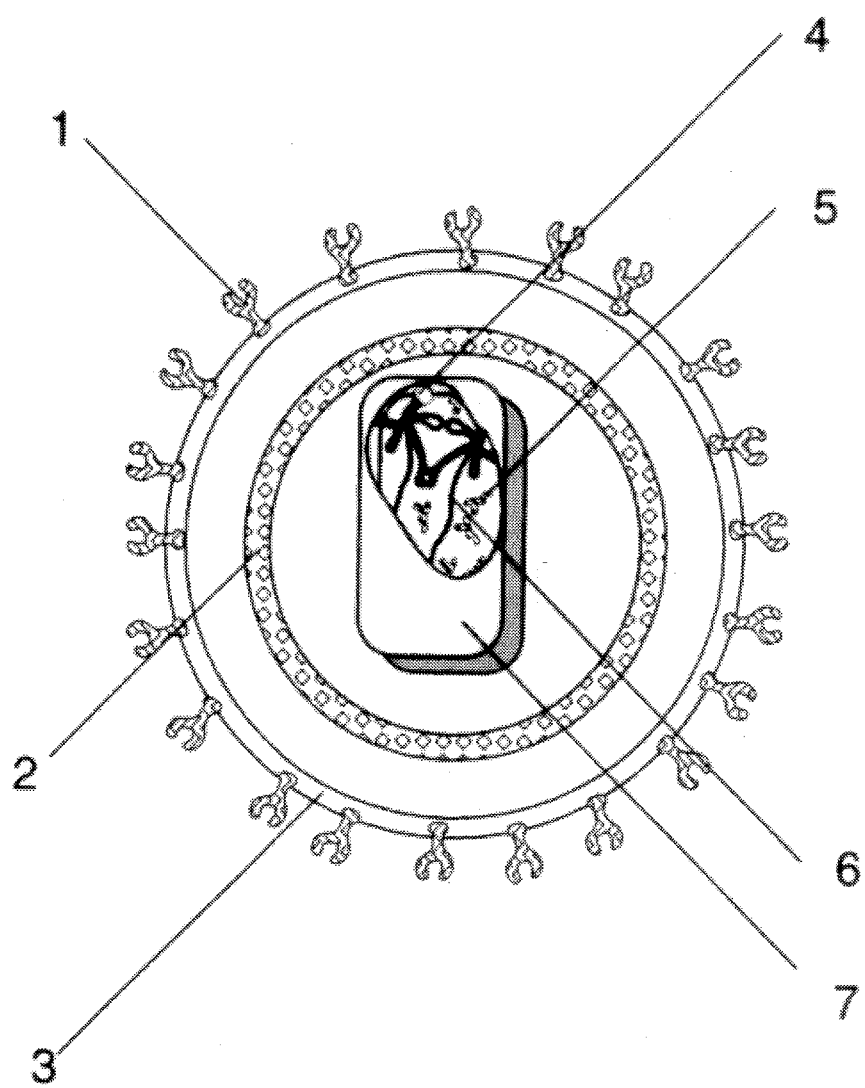
FIG. 7 is a schematic-drawing of the HIV virus.

Before turning to the experimental details it may be helpful to provide a brief description of the structure and replication of the HIV virus. Thus in FIG. 7 there are illustrated the gp120/gp41 coat glycoproteins (1) of HIV-1 virus disposed in the external lipid bilayer (3) which surrounds the viral core outer shell (2) which itself comprises p18 subunits. Within outer shell (2) is the inner core (7) which is made up of p24 subunits and within this the nucleocapsid gag protein (4), the RT enzyme (5) and the genomic RNA (6).

Figure 8:
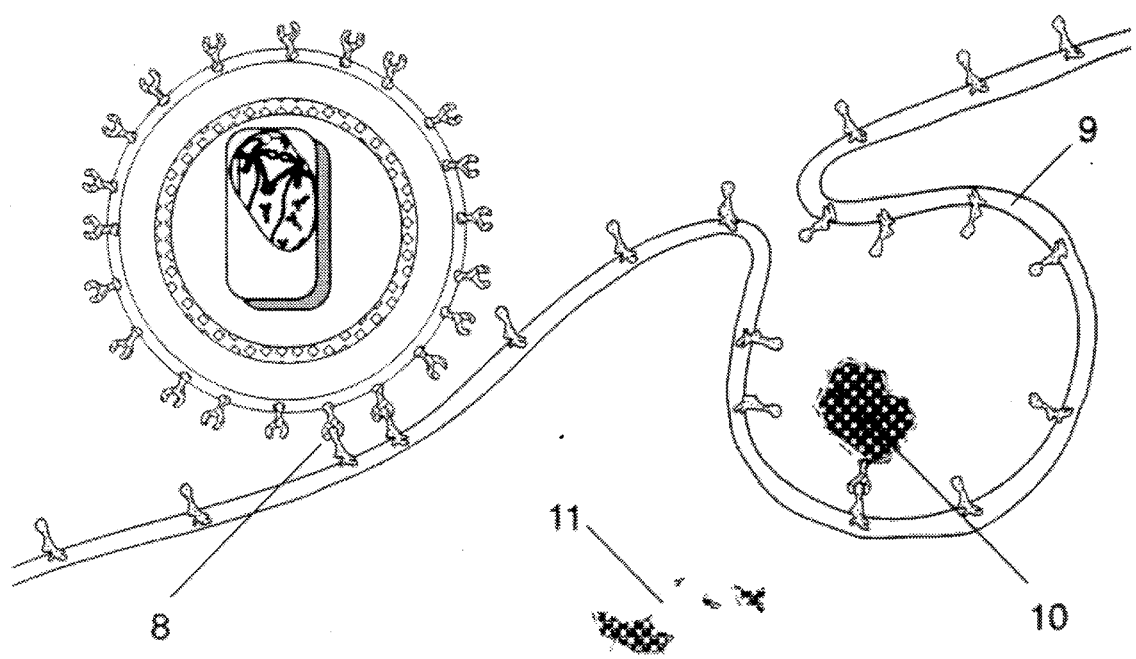
FIGS. 8 to 14 illustrate schematically stages of HIV infection and replication.
Figure 9:
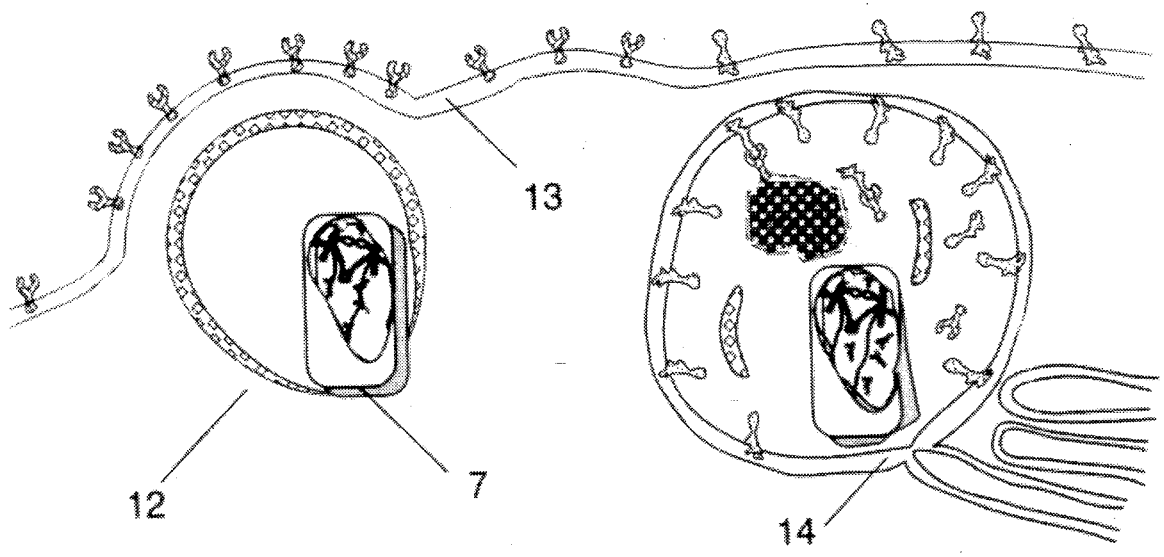

FIG. 8 shows the viral gp120 protein bound to CD4 protein (8) in the lipid bilayer (9) of a macrophage cell surface. The Figure also shows an intact palladium ferrite dextran coated particle (10) with conjugated gp120, being phagocytosed into an endosome, and a partially digested ferrite particle (11) in the macrophage. FIG. 9 illustrates the process of uncoating of the HIV viral genome inside a human macrophage, the partially uncoated virus (12) having lost the viral lipid coat which has fused with the cellular lipid coat (13). The Figure also illustrates an alternate entry path for virus after phagocytosis with subsequent uncoating into internal endoplasmic channels (14).

Figure 10:
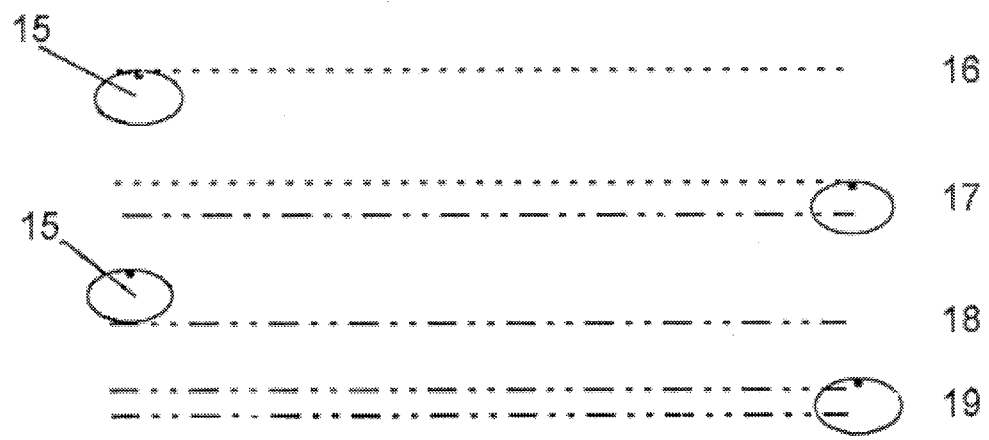

FIG. 10 provides a schematic indication of the role of metal cations in viral replication. Thus (15) indicates a metal cation bound to reverse transcriptase enzyme attached to genomic RNA strand (16). The metal/RT enzyme remains during completion of the RNA-dependent DNA polymerase step of reverse transcription (17) and remains attached to the DNA (18) during completion of the RNase H step to degrade the RNA template and the formation of the double stranded viral DNA (18) which is completed by DNA dependent DNA polymerase function of the reverse transcriptase enzyme.

Figure 11:
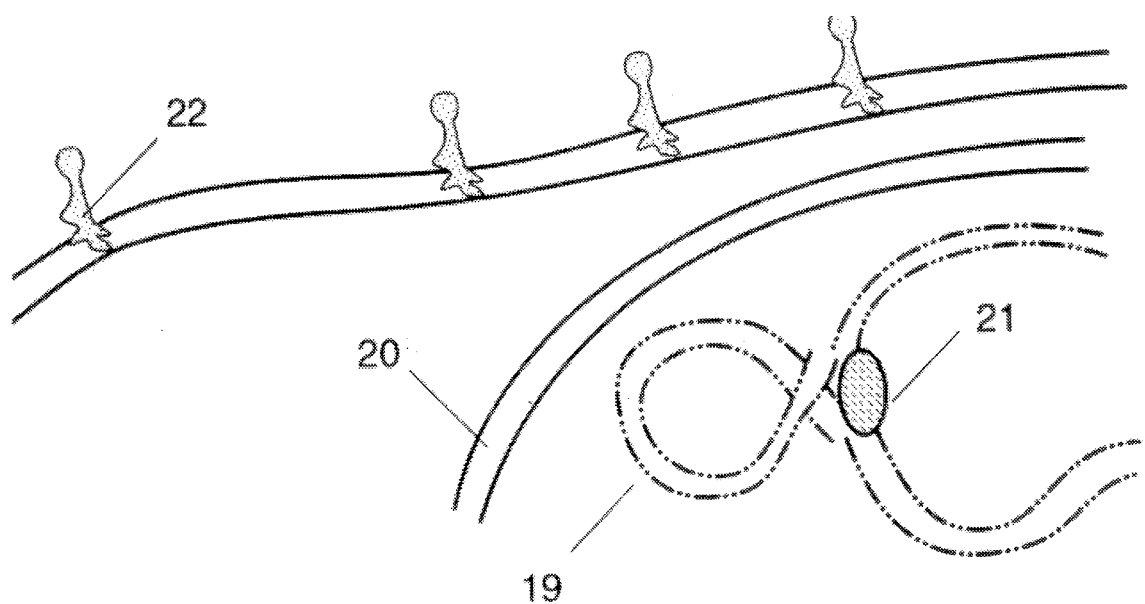
Figure 12:
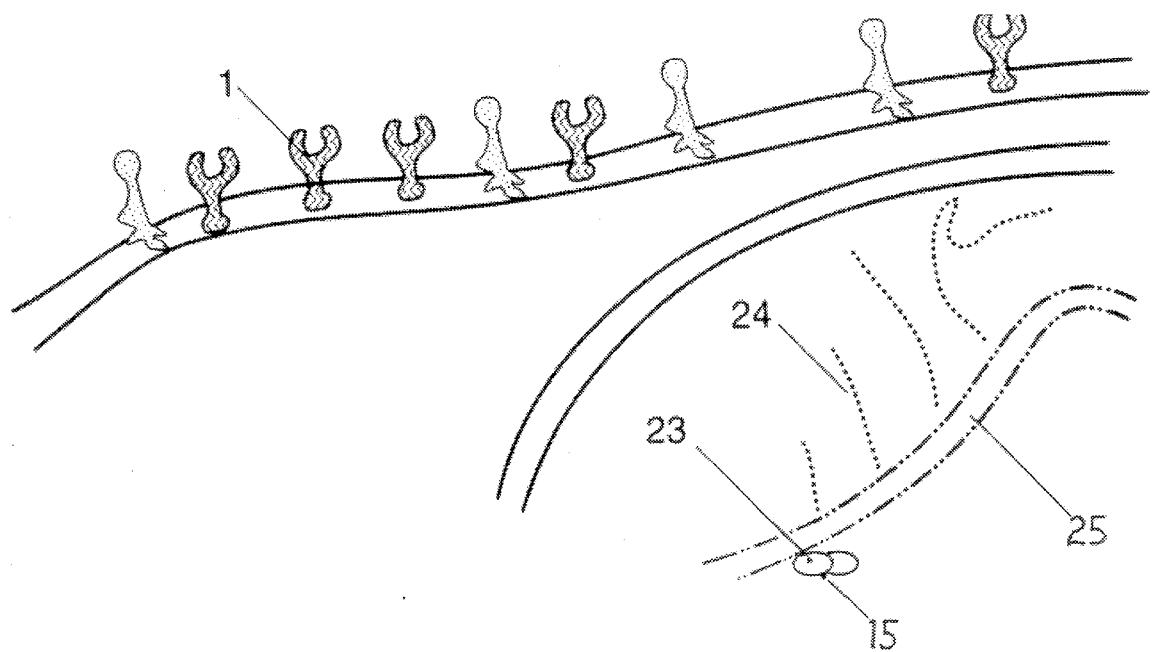

FIG. 11 shows the nuclear membrane (20) of the host cell with integrase protein (21) establishing provirus by inserting the viral DNA into the host DNA genome. The CD4 protein (22) in cell surface lipid bilayer is also shown. FIG. 12 illustrates the trans-activator of transcription (tat) protein (23) with metal cation (15) at the dimerization site and shows transcription of mRNA/genomic RNA (24) under control of tat as well as showing the integrated proviral DNA (25).

Figure 13:
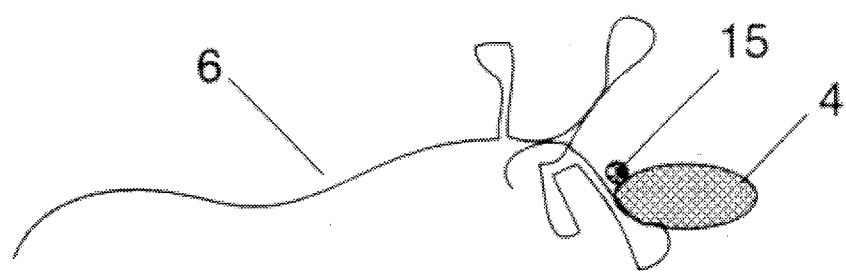
Figure 14:
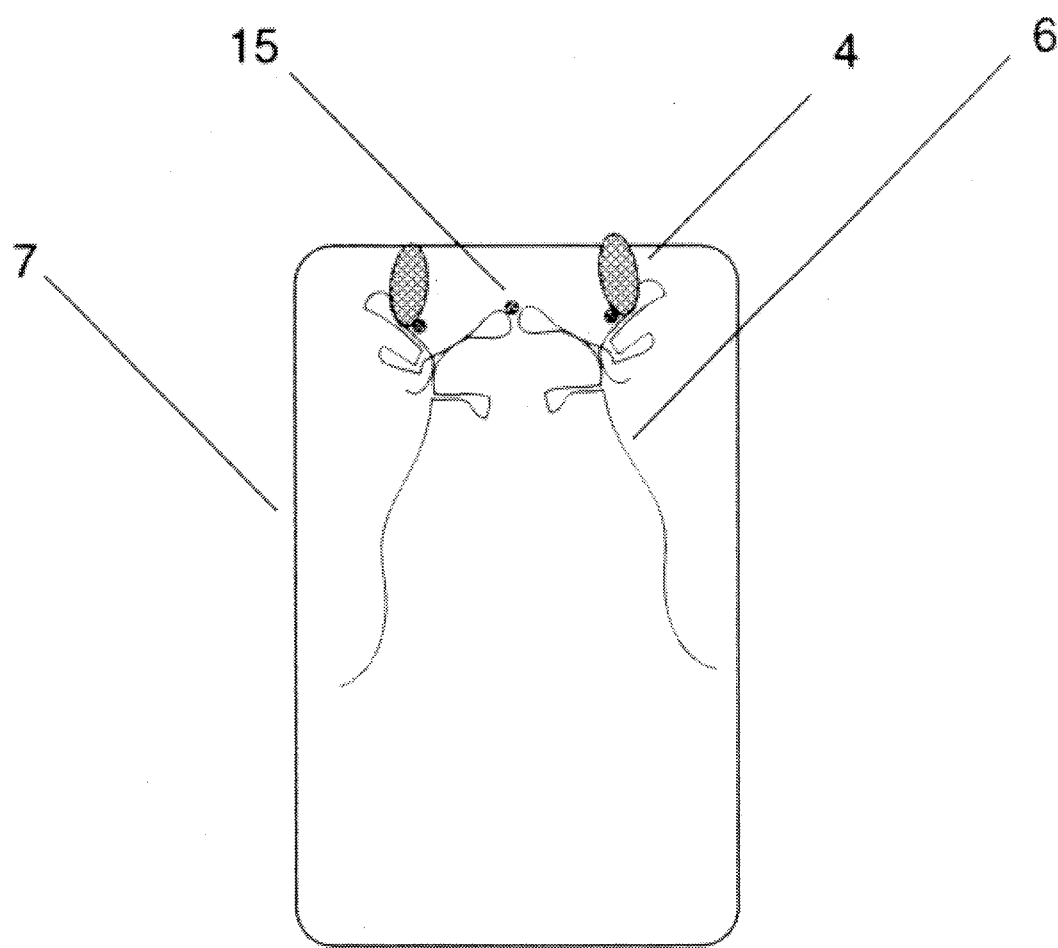

FIG. 13 shows how the nucleocapsid protein (4) binds the viral RNA (6). A metal cation (15) maintains the conformation at the nucleic acid binding site. In FIG. 14 it is shown how the nucleocapsid protein (4) is bound into the forming p24 inner core (7). The two copies of the genomic RNA (6) are attached to the capsid by the nucleocapsid protein. A cation (15) is involved at a dimerization site between the two RNA strands.

Reverse transcriptase (RT) assays with a wide variety of metal cations can be conducted by modifying the Potts (Supra) method to accommodate the special requirements for solubility imposed by the chemistry of the various elements. Dithiothreitol (DTT) or elevated pH causes immediate precipitation of transition metals so the suggestion of Temin et al (Nature 226: 1211–1213 (1970)) who showed good activity without DTT when assays were run at 0°–4° C. were followed and a buffer pH of 7.3 as tolerated by most of the cations and by the enzyme was used. Copper cations precipitate in HEPES buffer but not in Tris. Ferrous and ferric cations are insoluble at pH greater than 4.0 and so iron cannot be used in these assays without a "metal buffer" chelator at greatly reduced effective concentrations.

The inhibitory effects of copper, nickel, and zinc were similar to those found with RT from MoMuLV (Moloney Murine Leukemia Virus), but the palladium inhibition in MoMuLV was not reversed by magnesium. Also, the ability of higher concentrations of manganese to inhibit the HIV enzyme in the presence of magnesium was not seen in MOMULV.

In dextran coated particles for cationic cell therapy, ferric iron can be used to establish a spinel structured ceramic oxide crystal ($[Fe^{3+}]_2[Mt^{2+}]O_4$) and the divalent metal sites in the crystal fill entirely with the selected divalent cation ($Fe^{2+}$, $Mn^{2+}$, $Pd^{2+}$, or $Ni^{2+}$) or a stoichiometric mixture of elements. The crystal structures of some compounds have not been established but are probably either of garnet or perovskite type and the synthesis described produces a low yield in the desired size range. Each ferrite particle used in these trials contains about $10^5$–$10^6$ metal atoms so the concentration of 3 mM for the trivalent element used in the THP-1 experiment reflects a concentration of particles in the nanomolar range. Uptake studies with $^{59}Fe$ labelled particles show a rate of approximately $5 \times 10^2$ particles per THP-1 cell per hour over 2 hours. Since the particles are readily seen by electron microscopy, it was possible to directly confirm their presence both adherent to the cell surface and in intracellular locations in amounts consistent with the $^{59}Fe$ results. Intravenous injection of a bolus of 50 μMoles/kg of the particles revealed four hour vascular clearance in the rabbit primarily to spleen, marrow, liver and lung of 75% of the injected dose, closely reflecting human data for similar MR contrast agents (see Ranney, Ann. NY Acad Sci 507: 104–119 (1987)).

Figure 3:
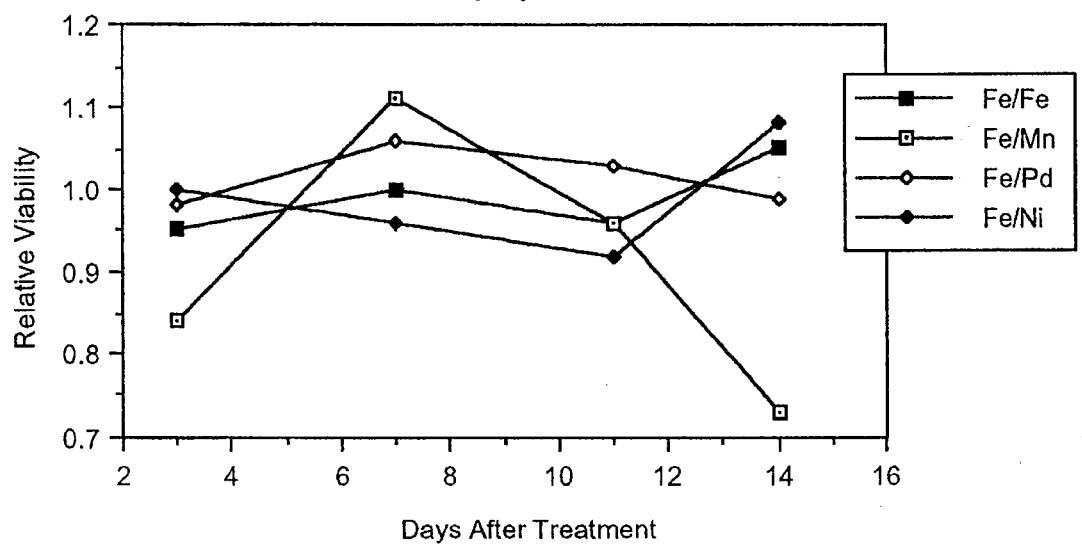
FIGS. 3 and 4 are graphs showing the effects of particles according to the invention on cell viability.
Figure 4:
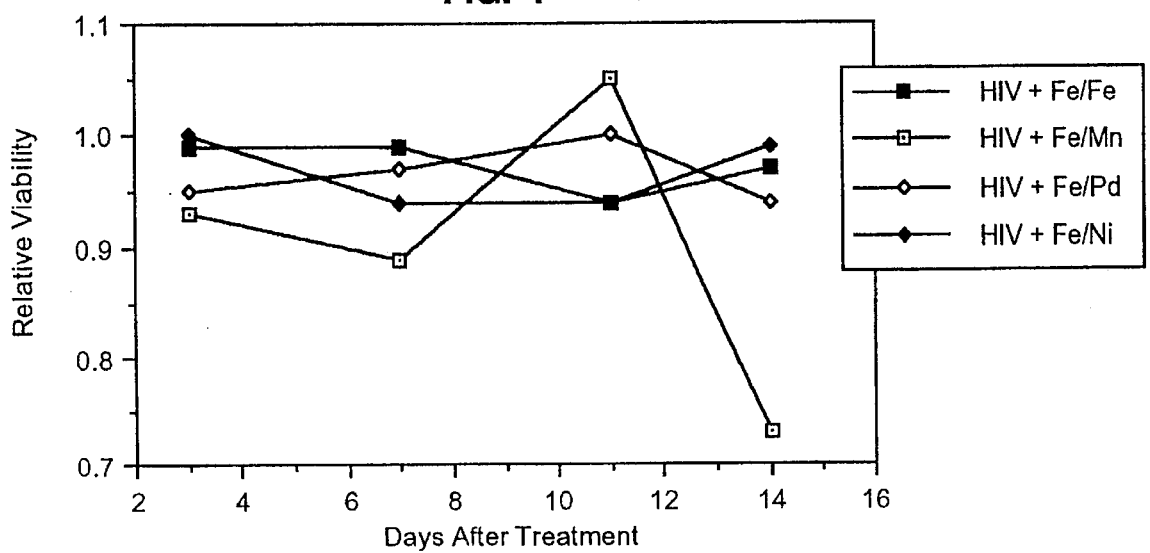

Only the Fe/Mn particles significantly affected THP-1 cell viability relative to either untreated, uninfected controls or relative to untreated, infected controls (see FIGS. 3 and 4). Both Fe/Mn and Fe/Pd particles effectively aborted the viral infection.

Cation source particles may be coated with dextran and conjugated to targeting proteins such as fragments of CD4 or of gp120. The dextran coat can be augmented or replaced with coatings which include co-active antiviral agents. However, there is a great potential for the use of simple, untargeted, dextran coated palladium ferrite particles for macrophage directed HIV treatment and acute prophylaxis.

Figure 1:
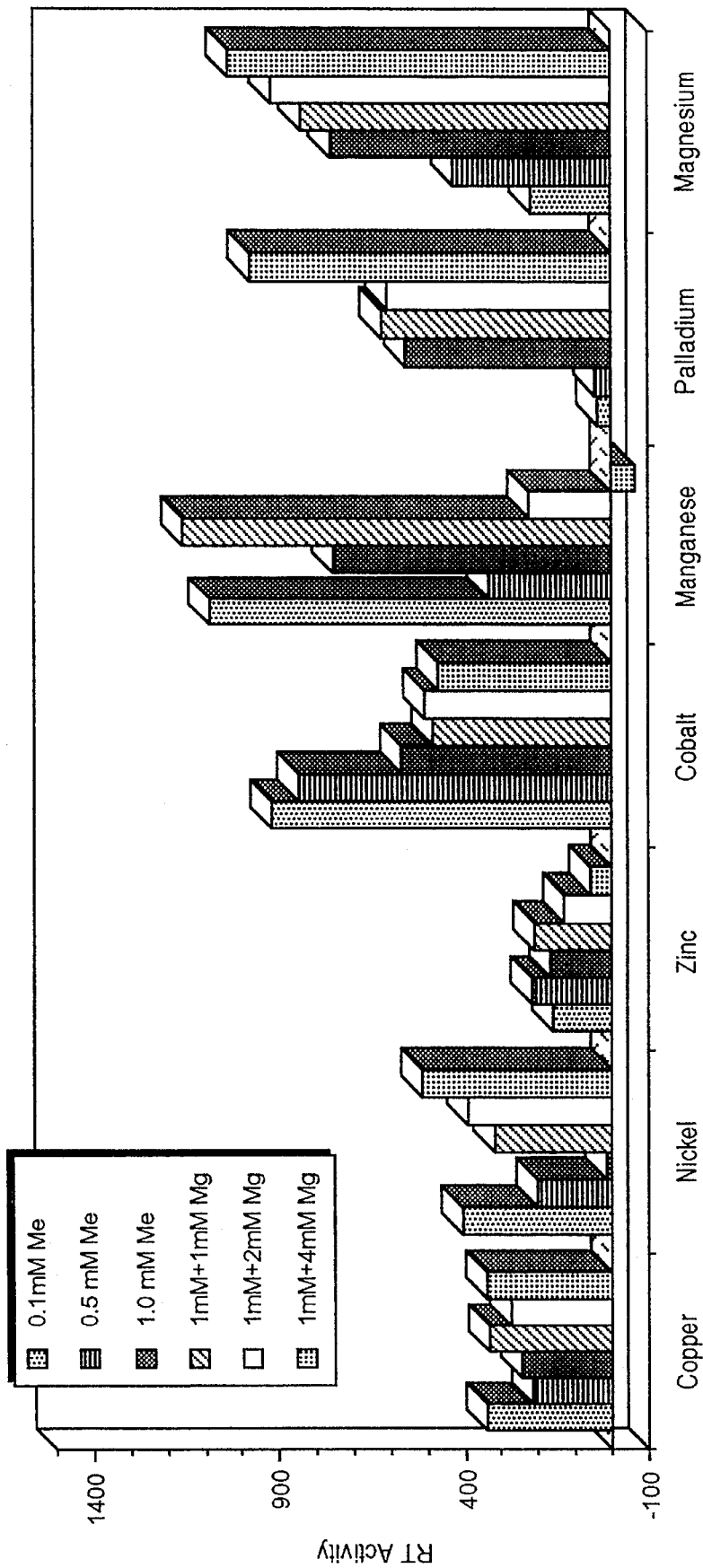
FIG. 1 is a graph indicating the effects on HIV-1 RT activity of a range of metal cations (Me) alone or in combination with magnesium.

FIG. 1 shows HIV-1 reverse transcriptase activity with divalent transition metals. Assays for FIG. 1 ran at 0°–4° C. with no DTT in 150 mM HEPES, pH7.3 except $Cu^{2+}$ which was run in 150 mM Tris, pH 7.5. The various complete buffers made in deionized, metal free water with 75 mM KCl, poly-rA 5 μg/ml, oligo $dT_{(12-18)}$ 5 μg/ml, peroxide free NP-40 0.05%, and [$^{32}P$]dTTp 5 μCi/ml. The various cocktails were transferred to 96 well plates in volumes of 100 μl/well, and the plates were then frozen. Metal solutions were prepared as 250 mM in 0.1 N HCl and serial dilutions then made in 0.1 N HCl to set up 96 well plates containing the various metals in the various final concentrations. The RT cocktail plates were then thawed and 20 μl of HIV infected cell free supernatant added to one set of plates while a control set received 20 μl of uninfected cell free supernatant from identical cultures and media, and an internal control well for each complete buffer channel received both 10 units of purified MoMuLV RT (Pharmacia) and 20 μl of cell free, uninfected supernatant. Reactions were started by transferring the various metal cation dilutions and $MgCl_2$ dilutions in 8 μl volumes to appropriate locations in HIV, MoMuLV, and control wells for each buffer/DTT/temperature condition using a multi-channel pipettor. 5 μl dot transfers to pre-numbered array locations on DE81 Whatman paper at 2 hours (34° C. plates) or at 4 hours (0°–4° C. plates) after start of the reaction were dried, washed, cut in squares and β-counted in 5 ml of scintillant. For this graph, activity from each control well is subtracted from the value for its corresponding assay well, MoMuLV internal controls are not shown, and only one magnesium value is shown for each temperature condition.

Figure 2:
FIG. 2 is an electron micrograph of a THP-1 (human macrophage) cell illustrating cellular uptake of particles according to the invention.

In FIG. 2 there is shown an electron micrograph section (60,000×) of a THP-1 cell (see Int. J. Cancer 76: 171–176 (1980)) showing ingested and surface adherent cation loaded particles. THP-1 cells were incubated at 37° C. for two hours with Fe/Pd dextran coated particles at a concentration equivalent to 3 mM $Fe^{3+}$ then washed, fixed in glutaraldehyde/PBS spun osmicated, embedded, and sectioned without staining. For each type of particle, 0.33 mMole of trivalent metal chloride hydrate and 0.17 mMole of divalent chloride hydrate (except $Fe^{2+}$ added as 0.20 mMole to account for oxidation before precipitation) were added directly to solutions made up by dissolving 500 mg 10,000 MW dextran in 750 μl of $H_2O$. $PdCl_2$ hydrates slowly so requires 12 hours in 4 N HCl (e.g. 100 μl for 35 mg of the chloride) to dissolve fully and is added as a solution to the dextran. 7.5% $NH_3$ solution is heated to 65° C. and after briefly heating each metal/dextran solution, 3 ml of the hot $NH_3$ solution added as six 500 μl aliquots for each mix, with 4 ml required for the Fe/Pd preparation. The precipitated, coated particles are incubated at 60° C. for one hour, during which the Fe/Pd solution gradually clears and the resulting suspensions then spun at 1,000 g×10 min twice to clear large particles. 1.5 ml of each solution is passed through a PD-10 Sephadex (Pharmacia) column equilibrated in 50 mM HEPES pH 7.4 buffering, to remove ammonia, and to clear unreacted ions. The 2.5 ml eluants are diluted to a volume of 14 ml with 50 mM HEPES pH 7.4 then concentrated in two steps in Centriprep-100 (Amicon) ultrafilters at 500 g×30 min, and 500 g×1 hour to a final volume of 0.5 ml to clear free dextran. These concentrates are then sterilized by 0.2 micron filtration with (Costar) 1 ml volume centrifugal microfilters at 3,000 g×1 hour. Final products were used for THP-1 infectivity trials and for EM studies (Fe/Fe and Fe/Pd). Similar Fe/Fe particles including $^{59}$Fe and subject to 0.1 micron filtration were used for THP-1 uptake studies and intravenous distribution/clearance assessment.

Figure 5:
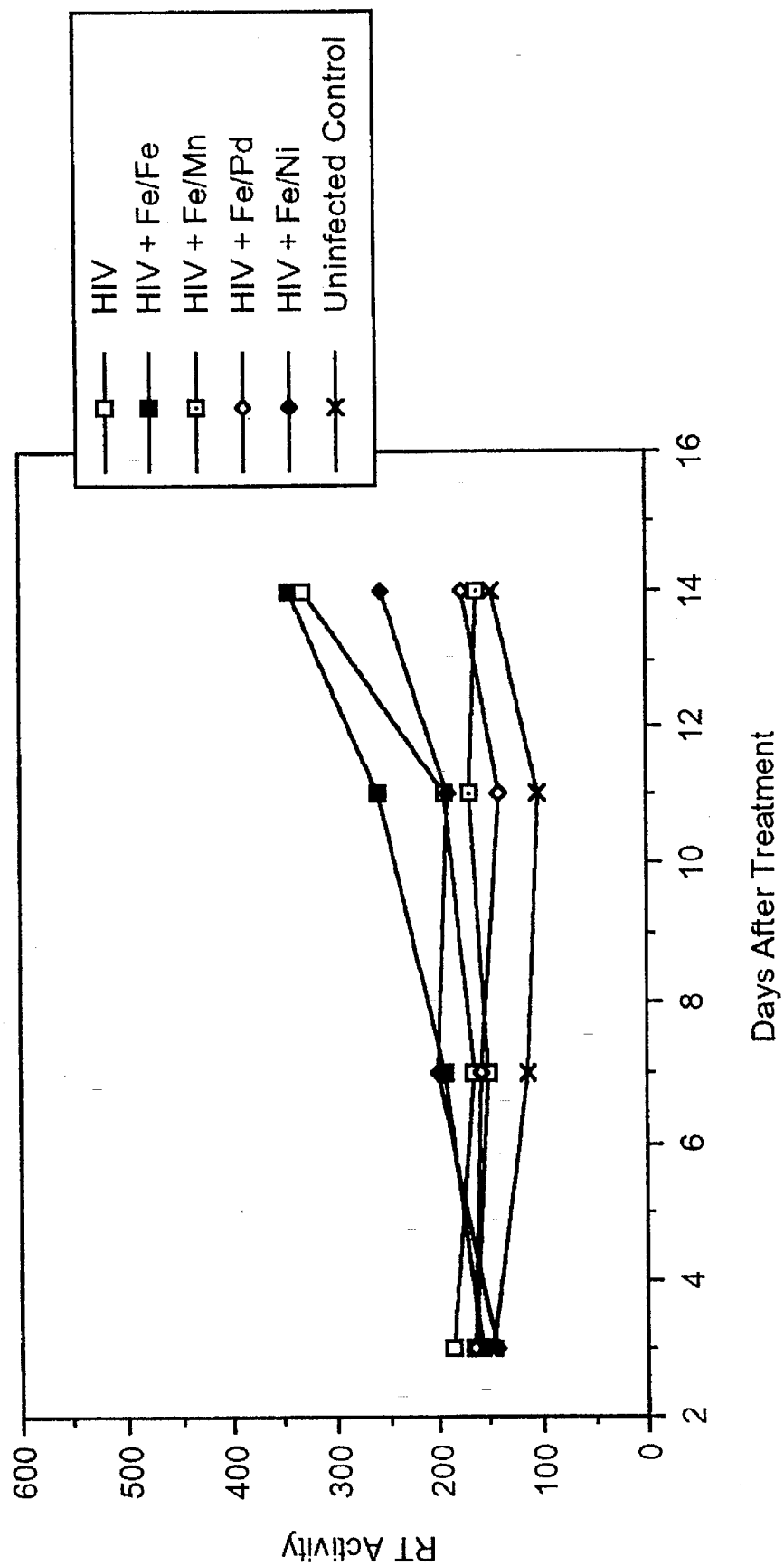
FIG. 5 is a graph showing the effects on HIV infection, as measured by HIV-1 RT activity, of cation cell therapy using different cations.
Figure 6:
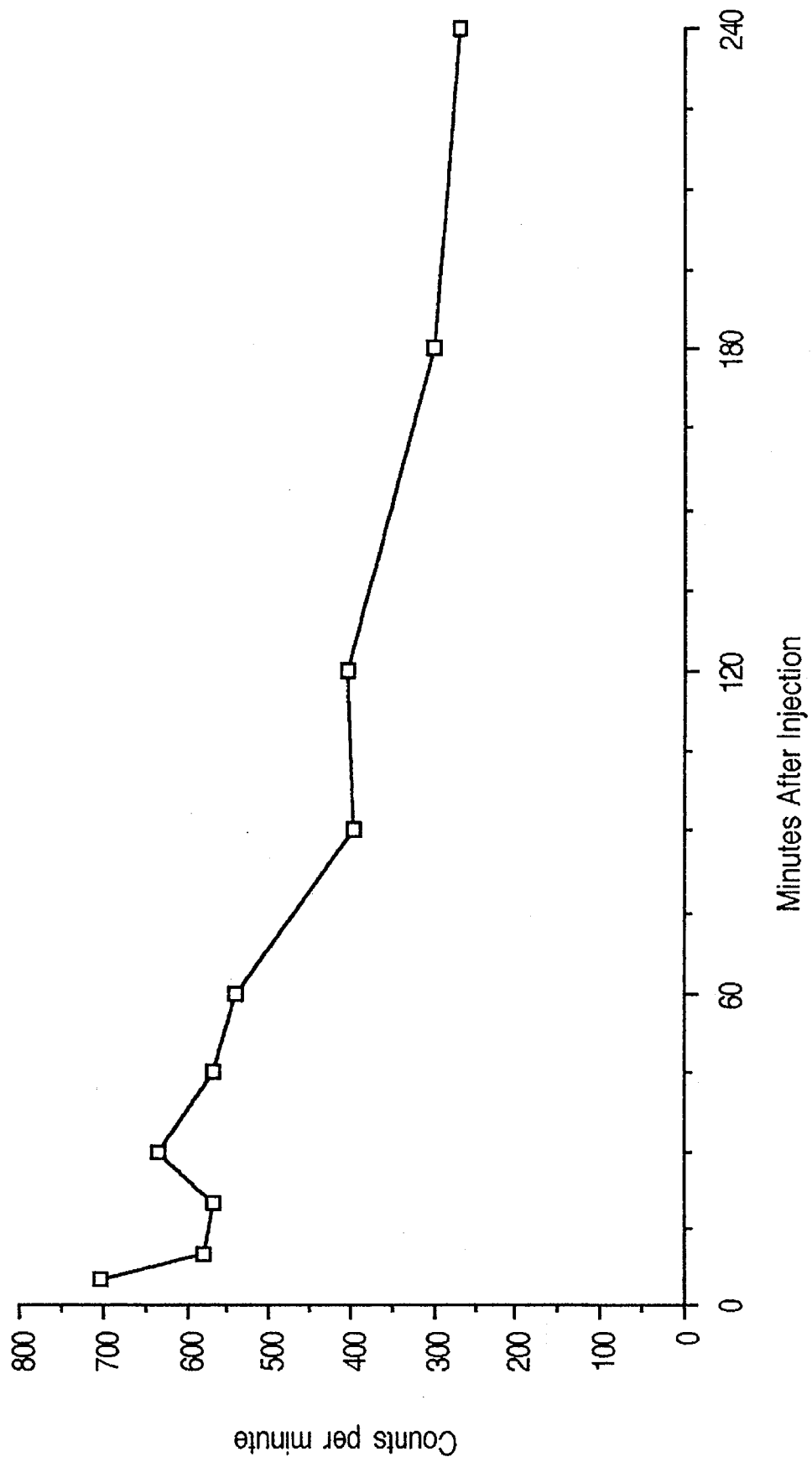
FIG. 6 is a graph illustrating the blood clearance rate for intravenously injected particles.

FIG. 3 shows the relative viability of cation source particle treated, uninfected compared to untreated, uninfected cells, and FIG. 4 shows the relative viability of treated, infected compared to untreated, infected cells. FIG. 5 shows RT assays (8 hours reaction time) from the various treatments. THP-1 cells were washed and incubated for two hours with one of four cation source particle suspensions at a concentration adjusted to be equivalent to 3 mM for the trivalent ferric cation (nanomolar particle concentrations) after which the cells were washed then seeded in 24 well microtitre plates at a concentration of 50,000 cells per well, four identical wells per metal and four control channels. After 24 hours, an aliquot of cells was withdrawn from each well to check viability and identical quantities of HIV RF strain then inoculated into two of each of the four wells in each group of cultures and incubated with regular medium changes. On days 3, 7, 11, and 14, aliquots of supernatant were withdrawn and stored at −70° C. for subsequent Potts (Supra) RT assay (dot transfers for counting were done after 2 hours and after 8 hours) and at the same time aliquots of cells were removed for total cell count and assessment of % viability by Trypan Blue exclusion.

We claim:

1. A particle comprising palladium disposed within an iron oxide matrix.

* * * * *